US011116731B2

(12) United States Patent
Kevil et al.

(10) Patent No.: US 11,116,731 B2
(45) Date of Patent: Sep. 14, 2021

(54) HYDROGEN SULFIDE AND/OR NITRITE IN THE TREATMENT AND PREVENTION OF ATRIAL FIBRILLATION

(71) Applicant: Board of Supervisors of Louisiana State University and Agricultural and Mechanical College, Baton Rouge, LA (US)

(72) Inventors: Christopher G. Kevil, Shreveport, LA (US); Paari Dominic, Baton Rouge, LA (US)

(73) Assignee: Brd. of Sup. of LSU and A &M College, Baton Rouge, LA (US)

( * ) Notice: Subject to any disclaimer, the term of this patent is extended or adjusted under 35 U.S.C. 154(b) by 0 days.

(21) Appl. No.: 16/486,596

(22) PCT Filed: Feb. 20, 2018

(86) PCT No.: PCT/US2018/018750
§ 371 (c)(1),
(2) Date: Aug. 16, 2019

(87) PCT Pub. No.: WO2018/152509
PCT Pub. Date: Aug. 23, 2018

(65) Prior Publication Data
US 2019/0365669 A1 Dec. 5, 2019

Related U.S. Application Data

(60) Provisional application No. 62/461,028, filed on Feb. 20, 2017.

(51) Int. Cl.
*A61K 31/10* (2006.01)
*A61P 9/06* (2006.01)
*A61K 33/00* (2006.01)
*A61K 36/8962* (2006.01)

(52) U.S. Cl.
CPC .............. *A61K 31/10* (2013.01); *A61K 33/00* (2013.01); *A61P 9/06* (2018.01)

(58) Field of Classification Search
CPC .... A61K 31/10; A61K 33/00; A61K 36/8962; A61P 9/06
See application file for complete search history.

(56) References Cited

U.S. PATENT DOCUMENTS

| | | |
|---|---|---|
| 5,112,598 A | 5/1992 | Biesalski |
| 5,556,611 A | 9/1996 | Biesalski |
| 2004/0110691 A1 | 6/2004 | Stamler |
| 2007/0154569 A1 | 7/2007 | Gladwin et al. |
| 2008/0299181 A1* | 12/2008 | Kannar ............... A61P 9/12 424/439 |
| 2014/0112983 A1* | 4/2014 | Giordano ............ A61K 36/88 424/457 |
| 2015/0233896 A1* | 8/2015 | Kevil ................. G01N 33/84 514/312 |
| 2016/0067279 A1 | 3/2016 | Kevil et al. |
| 2016/0081962 A1 | 3/2016 | Miller et al. |

FOREIGN PATENT DOCUMENTS

| | | |
|---|---|---|
| WO | 201325790 A2 | 2/2013 |
| WO | WO2014183108 | * 11/2014 |
| WO | 2015002612 A1 | 1/2015 |

OTHER PUBLICATIONS

Xu et al; PLOS One; Allitridi inhibits multiple cardiac potassium channels expressed in HEK 293 cells. vol. 7, Issue 12. pp. 1-10. Dec. 2012 (Year: 2012).*
G Lu et al., H2S Inhibits Angiotensin II-Induced Atrial Kv1.5 Upregulation by Attenuating Nox4-Mediated ROS Generation During Atrial Fibrillation, Biochem Biophys Res Commun, Jan. 29, 2017, vol. 483, No. 1, pp. 534-540, See International Search.
Y Zheng et al, Hydrogen Sulfide Prodrugs—Review, Acta Pharmaceutica Sinica B 2015, vol. 5, No. 5, pp. 367-377, See International Search.
DJ Polhemus et al., A Novel Hydrogen Sulfide Prodrug, SG1002, Promotes Hydrogen Sulfide and Nitric Oxide Bioavailability in Heart Failure Patients, Cardiovascular Therapeutics 2015, vol. 33, pp. 216-226, See International Search.
T Minamino et al., Plasma Levesl of Nitrite/Nitrate and Platelet cGMP Levels are Decreased in Patients with Atrial Fibrullation, Arteriosclerosis, Thrombosis, and Vascular Biology 1997, vol. 17, pp. 3191-3195, See International Search.
International Search Report Corresponding to PCT/US2018/018750 dated Apr. 13, 2018.
Written Opinion Corresponding to PCT/US2018/018750 dated Apr. 13, 2018.
Nitrite Therapy Ameliorates Myocardial Dysfunction via H2S and Nuclear Factor-Erythroid 2-Related Factor 2 (Nrf2)—Dependent Signaling in Chronic Heart Failure. doi:10.1161/JAHA.116.003551, Jan. 1, 2016.
Indian Office Action issued in corresponding Indian Patent Application No. 201927031470 dated Feb. 25, 2021.
Predmore , B.L. et al., "The polysulfide diallyl trisulfide protects the ischemic myocardium by preservation of endogenous hydrogen sulfide and increasing nitric oxide bioavailability.", Am J Physiol Heart Circ Physiol., Mar. 30, 2012, vol. 302, No. 11, pp. H2410-H2418.
Salloum, F.N. et al., "Beetroot juice reduces infarct size and improves cardiac function following ischemia-reperfusion injury: Possible involvement of endogenous H2S.", Exp Biol Med (Maywood), Oct. 30, 2014, vol. 240, No. 5, pp. 669-681.

(Continued)

*Primary Examiner* — Mina Haghighatian
(74) *Attorney, Agent, or Firm* — Holoubek Patent Law, L.L.C.; Charlotte Holoubek

(57) ABSTRACT

A method of treating Atrial Fibrillation or a pre-Atrial Fibrillation condition in a mammal, preferably a human, comprising administering a therapeutically effective amount of one of organic or inorganic sulfide, organic or inorganic nitrite, both organic or inorganic sulfide and organic or inorganic nitrite, or pharmacologically acceptable salts, solvates, esters, amides, clathrates, stereoisomers, enantiomers, prodrugs or analogs thereof, or a combination thereof.

10 Claims, 36 Drawing Sheets

(56) References Cited

OTHER PUBLICATIONS

Banerjee, S.K. et al., "Effect of garlic on cardiovascular disordersw: a review.", Nutrition Journal, Nov. 19, 2002, vol. 1, pp. 4(1-14).
Singapore Search Report issued in Singapore Patent Application No. 11201906931Q dated Dec. 23, 2020.
Xiao-Hui XU et al., "Allitridi Inhibits Multiple Cardiac Potassium Channels Expressed in HEK 293 Cells", PLOS One, vol. 7, No. 12, Dec. 14, 2012, p. e51550 [See EP Search Report].
Martin N et al., "Anti-arrhythmic profile of a garlic dialysate assayed in dogs and isloated atrial preparations", Journal of Ethnopharmacology, Elsevier Ireland LTD, IE, vol. 43, No. 1, Jun. 1, 1994, pp. 1-8 [See EP Search Report].
Guang-Zhen Zhong, "Hydrogen Sulfide—a potent multichannel anti-arrhythmic drug", Journal of Cardiovascular Disease Research, Jan. 1, 2010 [See EP Search Report].
European Search Report issued in corresponding European Patent Application No. 18754890.4 dated Nov. 27, 2020.

\* cited by examiner

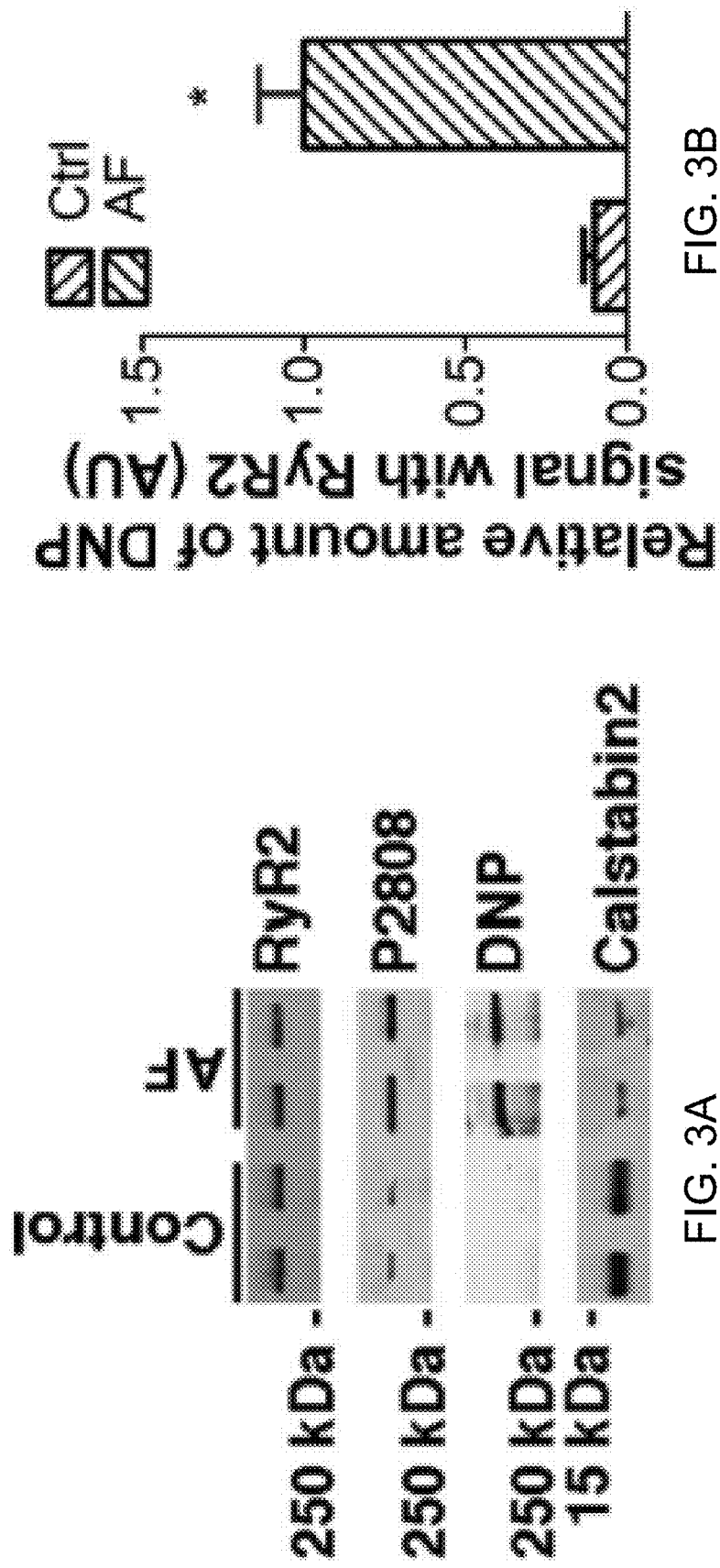

FIG. 4A
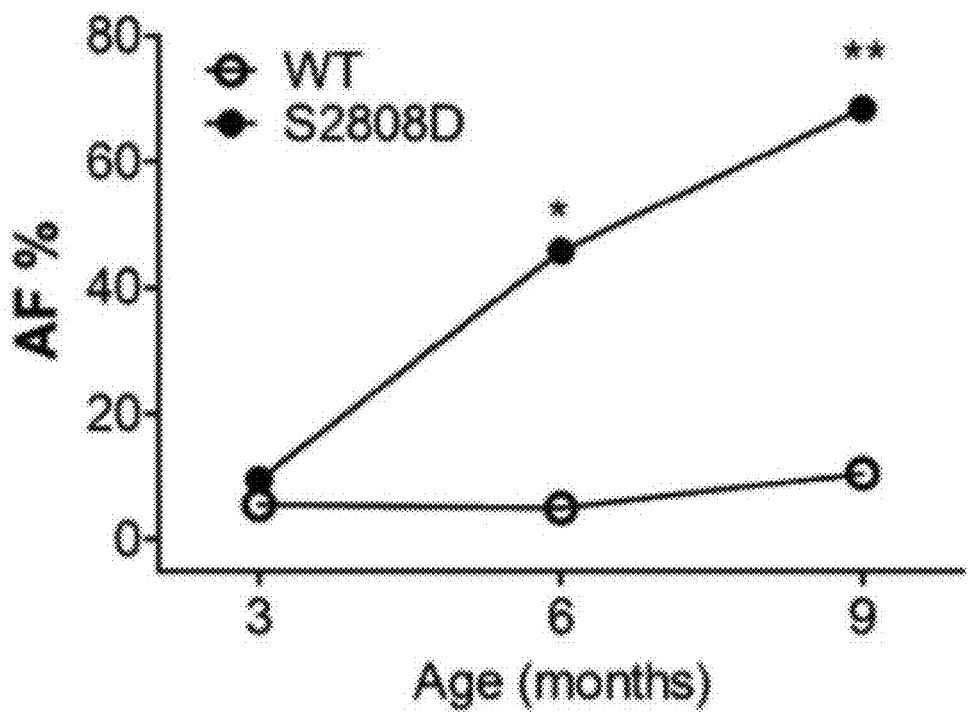
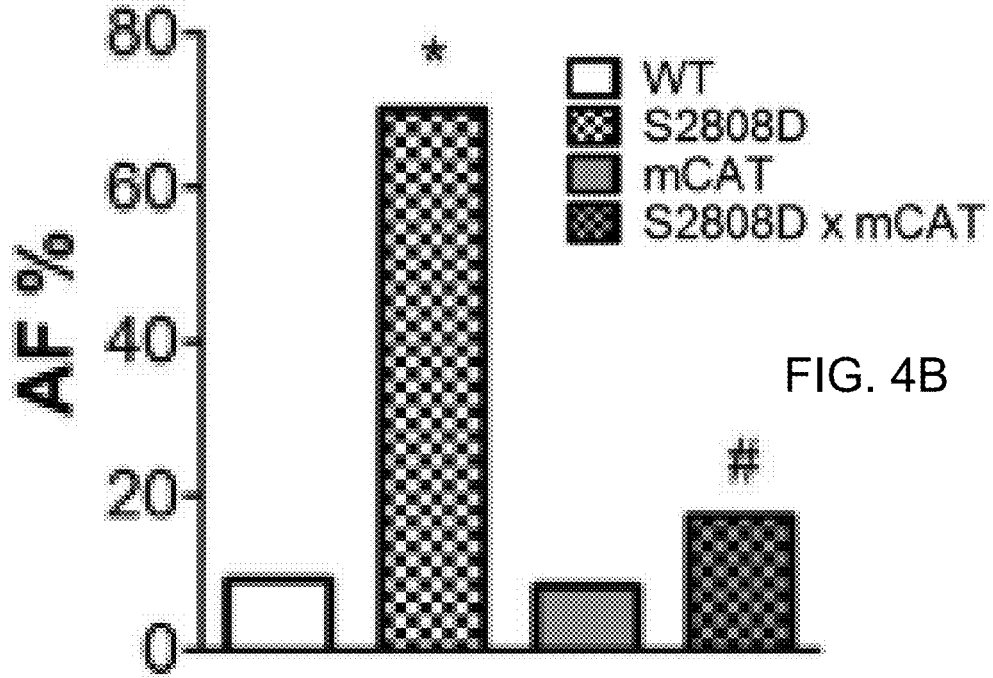
FIG. 4B

FIG. 5A  Hydrogen sulfide levels in heart failure patients
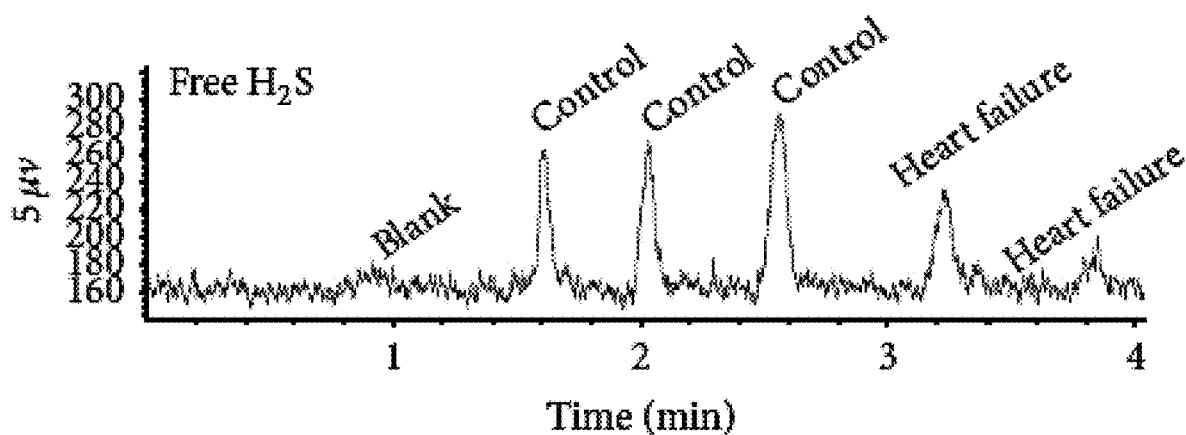
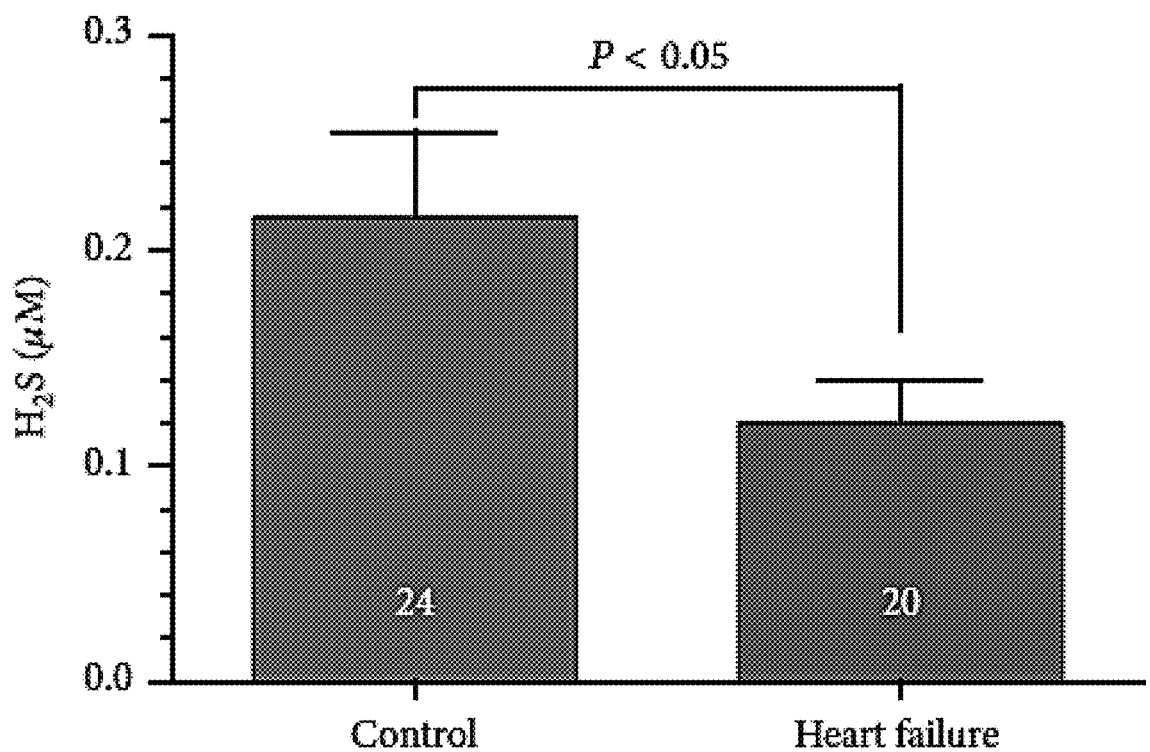
FIG. 5B

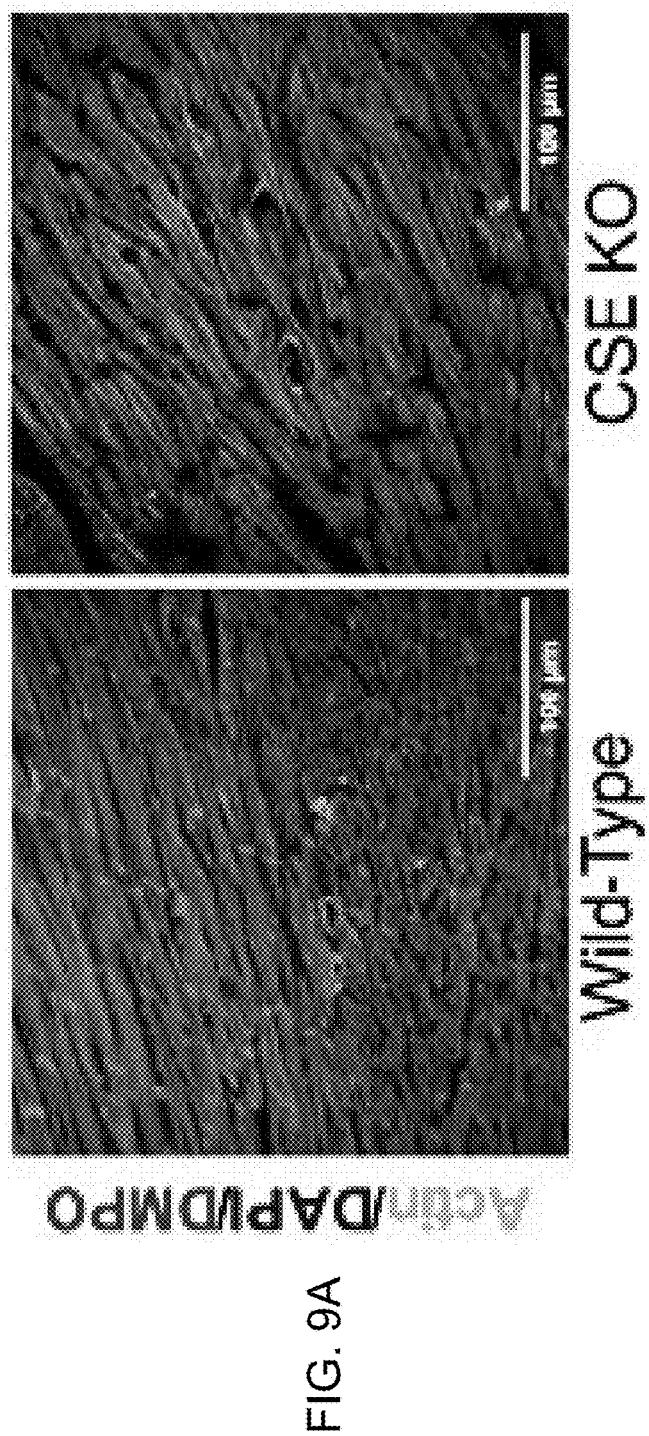
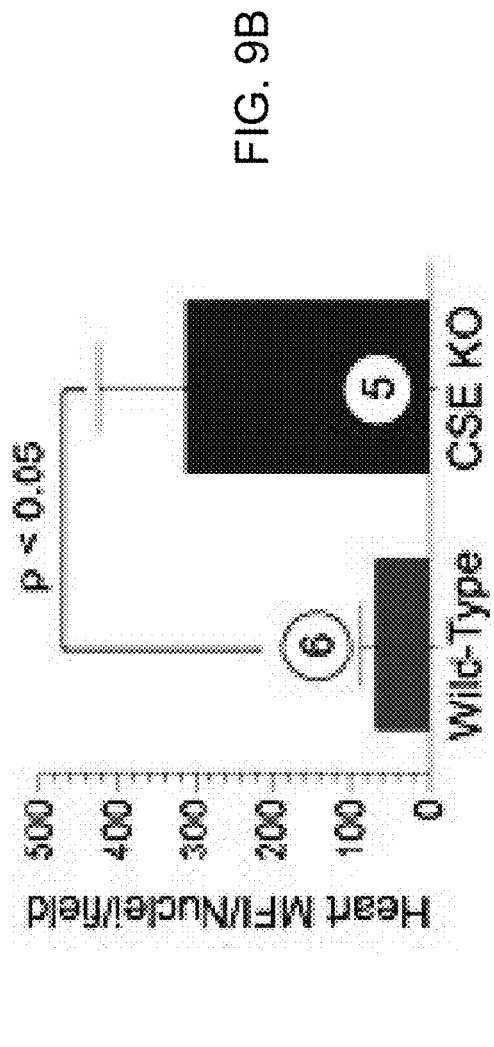
FIG. 9A
FIG. 9B

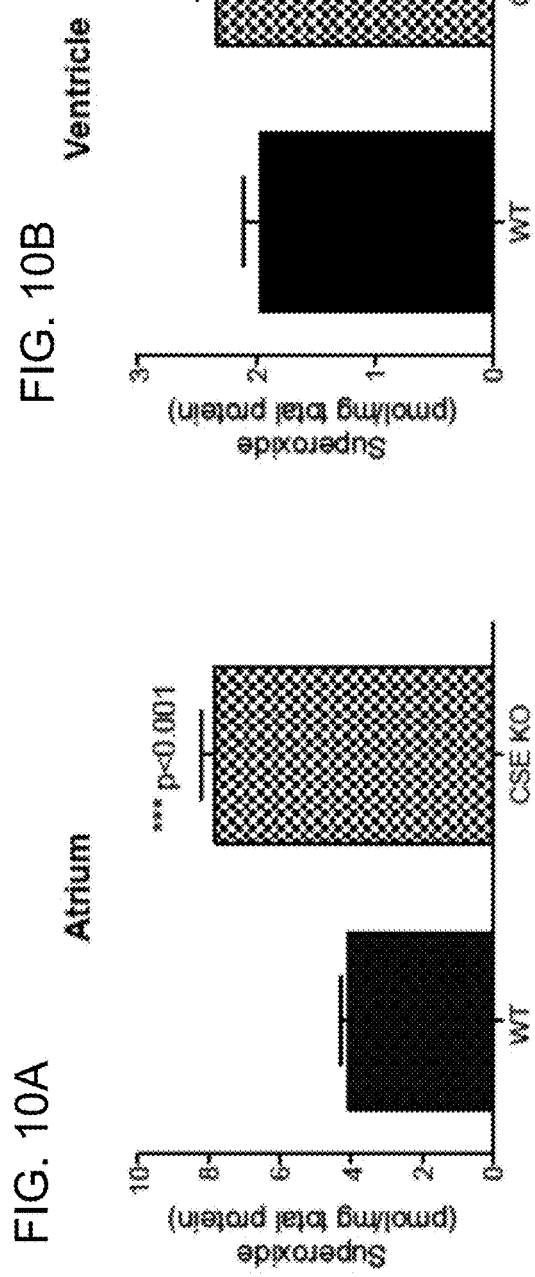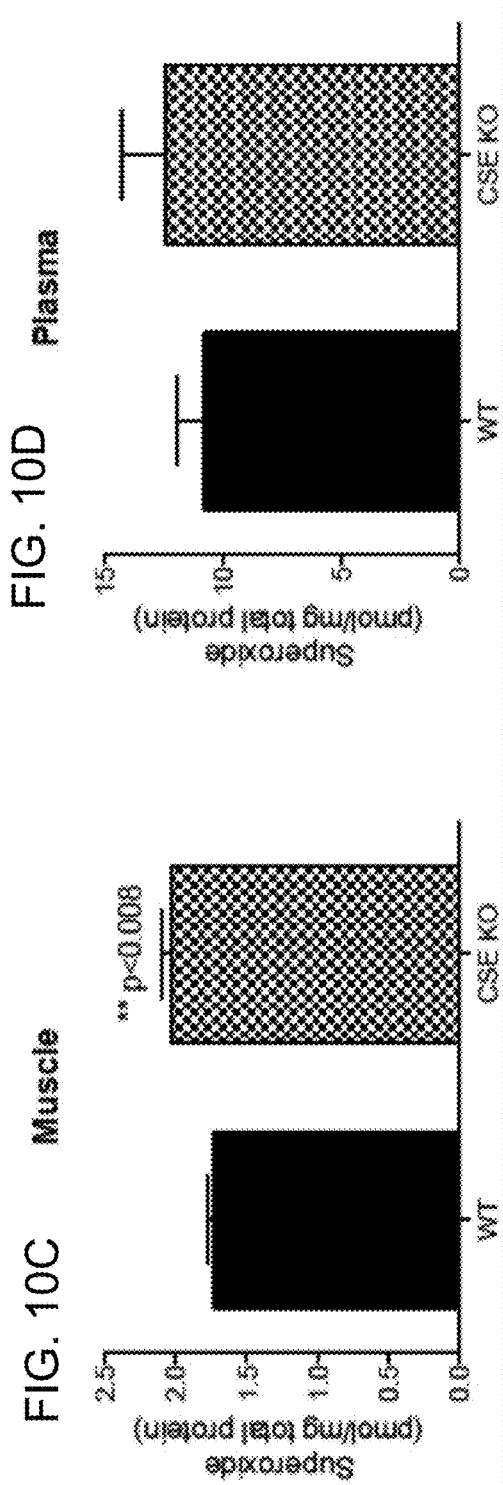

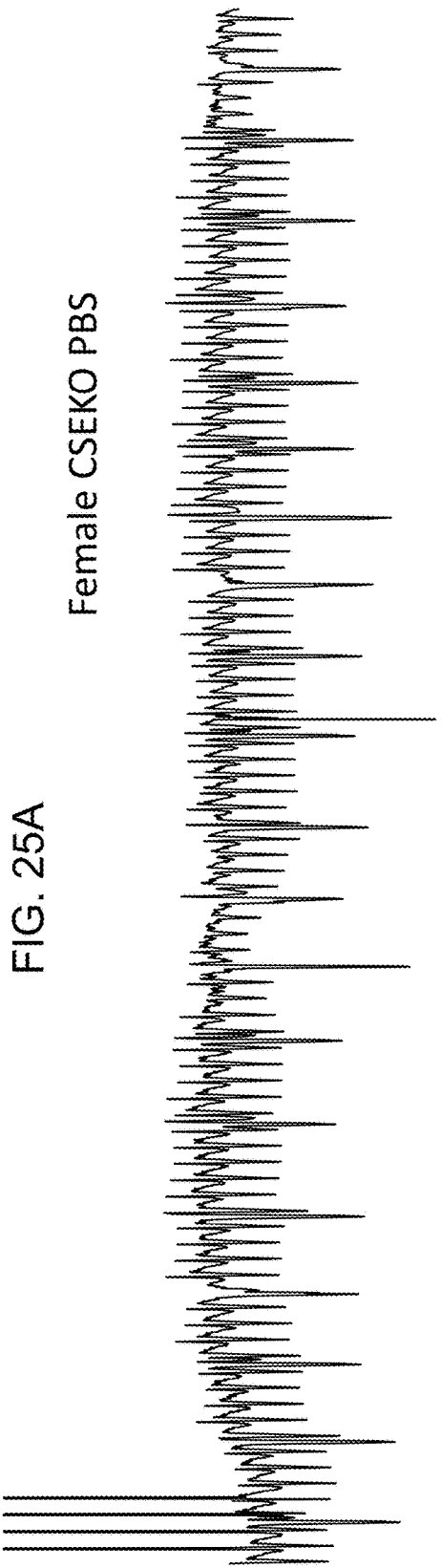
FIG. 25A Female CSEKO PBS
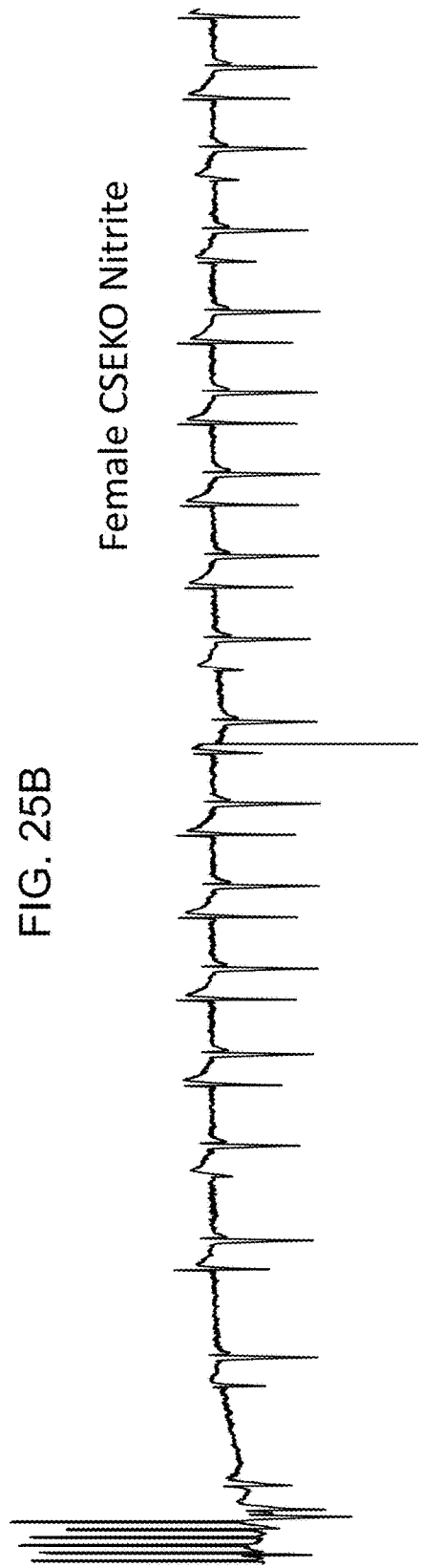
FIG. 25B Female CSEKO Nitrite

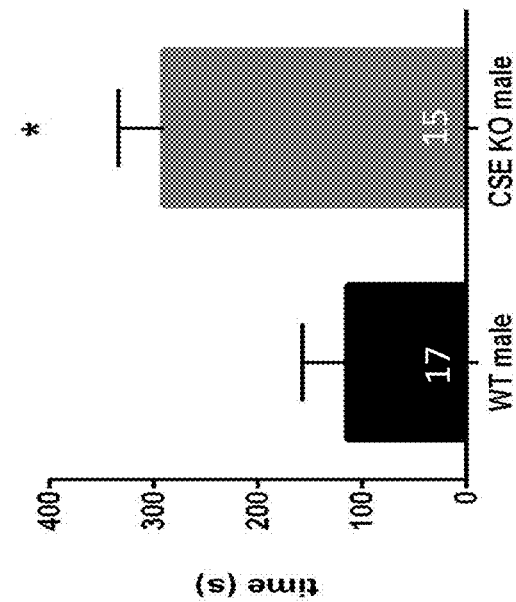
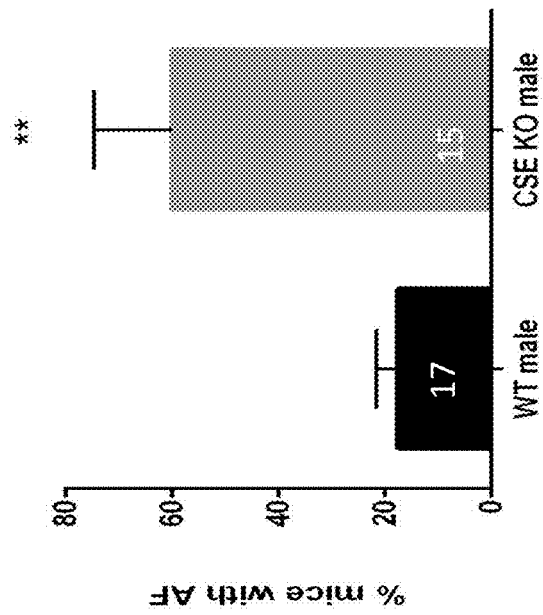

HYDROGEN SULFIDE AND/OR NITRITE IN THE TREATMENT AND PREVENTION OF ATRIAL FIBRILLATION

CROSS REFERENCE TO RELATED APPLICATIONS/PRIORITY

The present invention claims priority to U.S. Provisional Patent Application No. 62/461,028 filed Feb. 20, 2017, which is incorporated by reference into the present disclosure as if fully restated herein. Any conflict between the incorporated material and the specific teachings of this disclosure shall be resolved in favor of the latter. Likewise, any conflict between an art-understood definition of a word or phrase and a definition of the word or phrase as specifically taught in this disclosure shall be resolved in favor of the latter.

BACKGROUND OF THE INVENTION

Atrial fibrillation (AF) is a dysrhythmia of the heart where rapid and chaotic electrical activity in the atria (top chambers) of the heart causes irregular and rapid ventricular (bottom chambers) activity leading to heart failure and stroke. It has been estimated that 2.2 million people in the US and 4.5 million people in European Union suffer from AF with a prevalence that is estimated to at least double within the next 50 years. AF is the most common sustained cardiac arrhythmia. It currently affects about 1% of US population. In USA, 12-16 million will be affected by 2050. Increasing obesity and increasing age are risk factors that help explain rise in incidence. The lifetime risk of developing AF is expected to be one in four for men and women over 40 years of age.

Approximately eight ischemic strokes due to atrial fibrillation occur every hour in the US. In the US, there are approximately 795,000 new or recurrent strokes annually. Of these 87% are ischemic in nature, with the remaining 13% being hemorrhagic. Approximately 1 in 5 ischemic strokes is due to cardiogenic embolism. Of those, nonvalvular atrial fibrillation is responsible for about half. AF related ischemic strokes are more likely to cause a patient to be bedridden and to be disabling or fatal than non-AF-related ischemic strokes. Despite the overwhelming demand for treatment, including that that AF causes significant morbidity and mortality to a significant and growing portion of the population, and causes a significant and increasing the financial burden to the United States healthcare system, no sufficient treatment to AF has been presented in the prior art. For the foregoing reasons, there is a pressing, but seemingly irresolvable need for developing a treatment for AF and pre-AF conditions.

SUMMARY OF THE INVENTION

Wherefore, it is an object of the present invention to overcome the above mentioned shortcomings and drawbacks associated with the current technology.

The present invention also relates to treatments, therapeutics, kits, and methods of treating Atrial Fibrillation or a pre-Atrial Fibrillation condition in a mammal, preferably a human, comprising administering a therapeutically effective amount of one of organic or inorganic sulfide, organic or inorganic nitrite, both organic or inorganic sulfide and organic or inorganic nitrite, or pharmacologically acceptable salts, solvates, esters, amides, clathrates, stereoisomers, enantiomers, prodrugs or analogs thereof, or a combination thereof.

The present invention relates to pharmaceutical compositions of a therapeutic (e.g., organic and/or inorganic sulfide, organic and/or inorganic nitrite, or both organic and/or inorganic sulfide and organic and/or inorganic nitrite), or pharmaceutically acceptable salts, solvates, esters, amides, clathrates, stereoisomers, enantiomers, prodrugs or analogs thereof, or combination thereof, and use of these compositions for the treatment of AF or a pre-AF state.

In some embodiments, the therapeutic, or pharmaceutically acceptable salts, solvates, esters, amides, clathrates, stereoisomers, enantiomers, prodrugs or analogs thereof, or combination thereof, is administered as a pharmaceutical composition that further includes a pharmaceutically acceptable excipient.

In some embodiments, administration of the pharmaceutical composition to a human results in a peak plasma concentration of the therapeutic between 0.05 µM-10 µM (e.g., between 0.05 µM-5 µM).

In some embodiments, the peak plasma concentration of the therapeutic is maintained for up to 14 hours. In other embodiments, the peak plasma concentration of the therapeutic is maintained for up to 1 hour.

In some embodiments, the condition is AF or a pre-AF state.

In certain embodiments, the AF or a pre-AF state is mild to moderate AF or a pre-AF state.

In further embodiments, the AF or a pre-AF state is moderate to severe AF or a pre-AF state.

In other embodiments, the therapeutic is administered at a dose that is between 0.05 mg-5 mg/kg weight of the human.

In certain embodiments, the pharmaceutical composition is formulated for oral administration.

In other embodiments, the pharmaceutical composition is formulated for extended release.

In still other embodiments, the pharmaceutical composition is formulated for immediate release.

In some embodiments, the pharmaceutical composition is administered concurrently with one or more additional therapeutic agents for the treatment or prevention of the AF or a pre-AF state.

In some embodiments, the therapeutic, or pharmaceutically acceptable salts, solvates, esters, amides, clathrates, stereoisomers, enantiomers, prodrugs or analogs thereof, or combination thereof, is administered as a pharmaceutical composition that further includes a pharmaceutically acceptable excipient.

In some embodiments, administration of the pharmaceutical composition to a human results in a peak plasma concentration of the therapeutic between 0.05 µM-10 µM (e.g., between 0.05 µM-5 µM).

In some embodiments, the peak plasma concentration of the therapeutic is maintained for up to 14 hours. In other embodiments, the peak plasma concentration of the therapeutic is maintained for up to 1 hour.

In other embodiments, the therapeutic is administered at a dose that is between 0.05 mg-5 mg/kg weight of the human.

In certain embodiments, the pharmaceutical composition is formulated for oral administration.

In other embodiments, the pharmaceutical composition is formulated for extended release.

In still other embodiments, the pharmaceutical composition is formulated for immediate release.

As used herein, the term "delayed release" includes a pharmaceutical preparation, e.g., an orally administered formulation, which passes through the stomach substantially intact and dissolves in the small and/or large intestine (e.g., the colon). In some embodiments, delayed release of the active agent (e.g., a therapeutic as described herein) results from the use of an enteric coating of an oral medication (e.g., an oral dosage form).

The term an "effective amount" of an agent, as used herein, is that amount sufficient to effect beneficial or desired results, such as clinical results, and, as such, an "effective amount" depends upon the context in which it is being applied.

The terms "extended release" or "sustained release" interchangeably include a drug formulation that provides for gradual release of a drug over an extended period of time, e.g., 6-12 hours or more, compared to an immediate release formulation of the same drug. Preferably, although not necessarily, results in substantially constant blood levels of a drug over an extended time period that are within therapeutic levels and fall within a peak plasma concentration range that is between, for example, 0.05-10 µM, 0.1-10 µM, 0.1-5.0 µM, or 0.1-1 µM.

As used herein, the terms "formulated for enteric release" and "enteric formulation" include pharmaceutical compositions, e.g., oral dosage forms, for oral administration able to provide protection from dissolution in the high acid (low pH) environment of the stomach. Enteric formulations can be obtained by, for example, incorporating into the pharmaceutical composition a polymer resistant to dissolution in gastric juices. In some embodiments, the polymers have an optimum pH for dissolution in the range of approx. 5.0 to 7.0 ("pH sensitive polymers"). Exemplary polymers include methacrylate acid copolymers that are known by the trade name Eudragit® (e.g., Eudragit® L100, Eudragit® S100, Eudragit® L-30D, Eudragit® FS 30D, and Eudragit® L100-55), cellulose acetate phthalate, cellulose acetate trimellitiate, polyvinyl acetate phthalate (e.g., Coateric®), hydroxyethylcellulose phthalate, hydroxypropyl methylcellulose phthalate, or shellac, or an aqueous dispersion thereof. Aqueous dispersions of these polymers include dispersions of cellulose acetate phthalate (Aquateric®) or shellac (e.g., MarCoat 125 and 125N). An enteric formulation reduces the percentage of the administered dose released into the stomach by at least 50%, 60%, 70%, 80%, 90%, 95%, or even 98% in comparison to an immediate release formulation. Where such a polymer coats a tablet or capsule, this coat is also referred to as an "enteric coating."

The term "immediate release" includes where the agent (e.g., therapeutic), as formulated in a unit dosage form, has a dissolution release profile under in vitro conditions in which at least 55%, 65%, 75%, 85%, or 95% of the agent is released within the first two hours of administration to, e.g., a human. Desirably, the agent formulated in a unit dosage has a dissolution release profile under in vitro conditions in which at least 50%, 65%, 75%, 85%, 90%, or 95% of the agent is released within the first 30 minutes, 45 minutes, or 60 minutes of administration.

The term "pharmaceutical composition," as used herein, includes a composition containing a compound described herein (e.g., organic and/or inorganic sulfide, organic and/or inorganic nitrite, or both organic and/or inorganic sulfide and organic and/or inorganic nitrite, or any pharmaceutically acceptable salts, solvates, esters, amides, clathrates, stereoisomers, enantiomers, prodrugs or analogs thereof, or combination thereof), formulated with a pharmaceutically acceptable excipient, and typically manufactured or sold with the approval of a governmental regulatory agency as part of a therapeutic regimen for the treatment of disease in a mammal.

Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, includes any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, maltose, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable prodrugs" as used herein, includes those prodrugs of the compounds of the present invention which are, within the scope of sound medical judgment, suitable for use in contact with the tissues of humans and animals with undue toxicity, irritation, allergic response, and the like, commensurate with a reasonable benefit/risk ratio, and effective for their intended use, as well as the zwitterionic forms, where possible, of the compounds of the invention.

The term "pharmaceutically acceptable salt," as use herein, includes those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds of the invention or separately by reacting the free base group with a suitable organic or inorganic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The terms "pharmaceutically acceptable solvate" or "solvate," as used herein, includes a compound of the invention wherein molecules of a suitable solvent are incorporated in the crystal lattice. A suitable solvent is physiologically tolerable at the administered dose. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

The term "prevent," as used herein, includes prophylactic treatment or treatment that prevents one or more symptoms or conditions of a disease, disorder, or conditions described herein (e.g., AF or a pre-AF state). Treatment can be initiated, for example, prior to ("pre-exposure prophylaxis") or following ("post-exposure prophylaxis") an event that precedes the onset of the disease, disorder, or conditions. Treatment that includes administration of a compound of the invention, or a pharmaceutical composition thereof, can be acute, short-term, or chronic. The doses administered may be varied during the course of preventive treatment.

The term "prodrug," as used herein, includes compounds which are rapidly transformed in vivo to the parent compound of the above formula. Prodrugs also encompass bioequivalent compounds that, when administered to a human, lead to the in vivo formation of therapeutic. A thorough discussion is provided in T. Higuchi and V. Stella, Pro-drugs as Novel Delivery Systems, Vol. 14 of the A.C.S. Symposium Series, and Edward B. Roche, ed., Bioreversible Carriers in Drug Design, American Pharmaceutical Association and Pergamon Press, 1987, each of which is incorporated herein by reference. Prodrugs may also include foods, as listed below. Preferably, prodrugs of the compounds of the present invention are pharmaceutically acceptable.

As used herein, and as well understood in the art, "treatment" includes an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e. not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Treatment" can also mean prolonging survival as compared to expected survival if not receiving treatment. As used herein, the terms "treating" and "treatment" can also include delaying the onset of, impeding or reversing the progress of, or alleviating either the disease or condition to which the term applies, or one or more symptoms of such disease or condition.

The term "unit dosage forms" includes physically discrete units suitable as unitary dosages for human subjects and other mammals, each unit containing a predetermined quantity of active material calculated to produce the desired therapeutic effect, in association with any suitable pharmaceutical excipient or excipients.

As used herein, the term "plasma concentration" includes the amount of therapeutic present in the plasma of a treated subject (e.g., as measured in a rabbit using an assay described below or in a human).

Various objects, features, aspects, and advantages of the present invention will become more apparent from the following detailed description of preferred embodiments of the invention, along with the accompanying drawings in which like numerals represent like components. The present invention may address one or more of the problems and deficiencies of the current technology discussed above. However, it is contemplated that the invention may prove useful in addressing other problems and deficiencies in a number of technical areas. Therefore the claimed invention should not necessarily be construed as limited to addressing any of the particular problems or deficiencies discussed herein.

BRIEF DESCRIPTION OF THE DRAWINGS

The accompanying drawings, which are incorporated in and constitute a part of the specification, illustrate various embodiments of the invention and together with the general description of the invention given above and the detailed description of the drawings given below, serve to explain the principles of the invention. It is to be appreciated that the accompanying drawings are not necessarily to scale since the emphasis is instead placed on illustrating the principles of the invention. The invention will now be described, by way of example, with reference to the accompanying drawings in which:

FIGS. 3A and 3B show oxidation of calcium signaling proteins and AF-RyR.

FIG. 3A shows post-translational modifications of the RyR2 complex in right atrial (RA) tissue of patients with AF and normal ventricular function or controls. RA appendage tissue was obtained at the time of cardiac surgery from patients with chronic AF (>6 months; n=10), and patients in sinus rhythm (n=10). To determine RyR2 channel oxidation, the carbonyl groups in the protein side chains of immunoprecipitated RyR2 were derivatized to (DNP) by reaction with 2,4-dinitrophenylhydrazine. The DNP (2,4-dinitrophenylhydrazone) signal associated with RyR2 was determined by anti-DNP antibody. FIG. 3B show Quantification of DNP signal mice harboring an RyR2 mutation linked to human CPVT (RyR2-R2474S+/−) and mice expressing a phosphomimetic aspartic acid residue at position 2808 (RyR2-S2808D+/+) leading to constitutively leaky channels.

FIGS. 4A and 4B show percent AF by age (4A) and by subgroup (4B) of the mice in FIGS. 3A and 3B.

FIGS. 5A and 5B are a line graph and a bar chart showing hydrogen sulfide levels in heart failure patients.

FIGS. 9A and 9B are micrographs (9A) and is a bar graph (9B) showing oxidative stress with CSE KO mice.

FIGS. 10A to 10D are bar graphs showing super oxide levels in WT and CSE KO mice for atrium (10A), ventricle (10B), muscle (10C) and plasma (10D).

FIGS. 25A and 25B are electro cardio rhythms of CSE KO female mice PBS (25A) and Nitrite treated (25B).

FIGS. 28A and 28B are bar graphs showing persistent AF (28A) and duration of any AF (28B) in WT and CSE KO male mice.

DETAILED DESCRIPTION OF THE PREFERRED EMBODIMENTS

Figure 1:
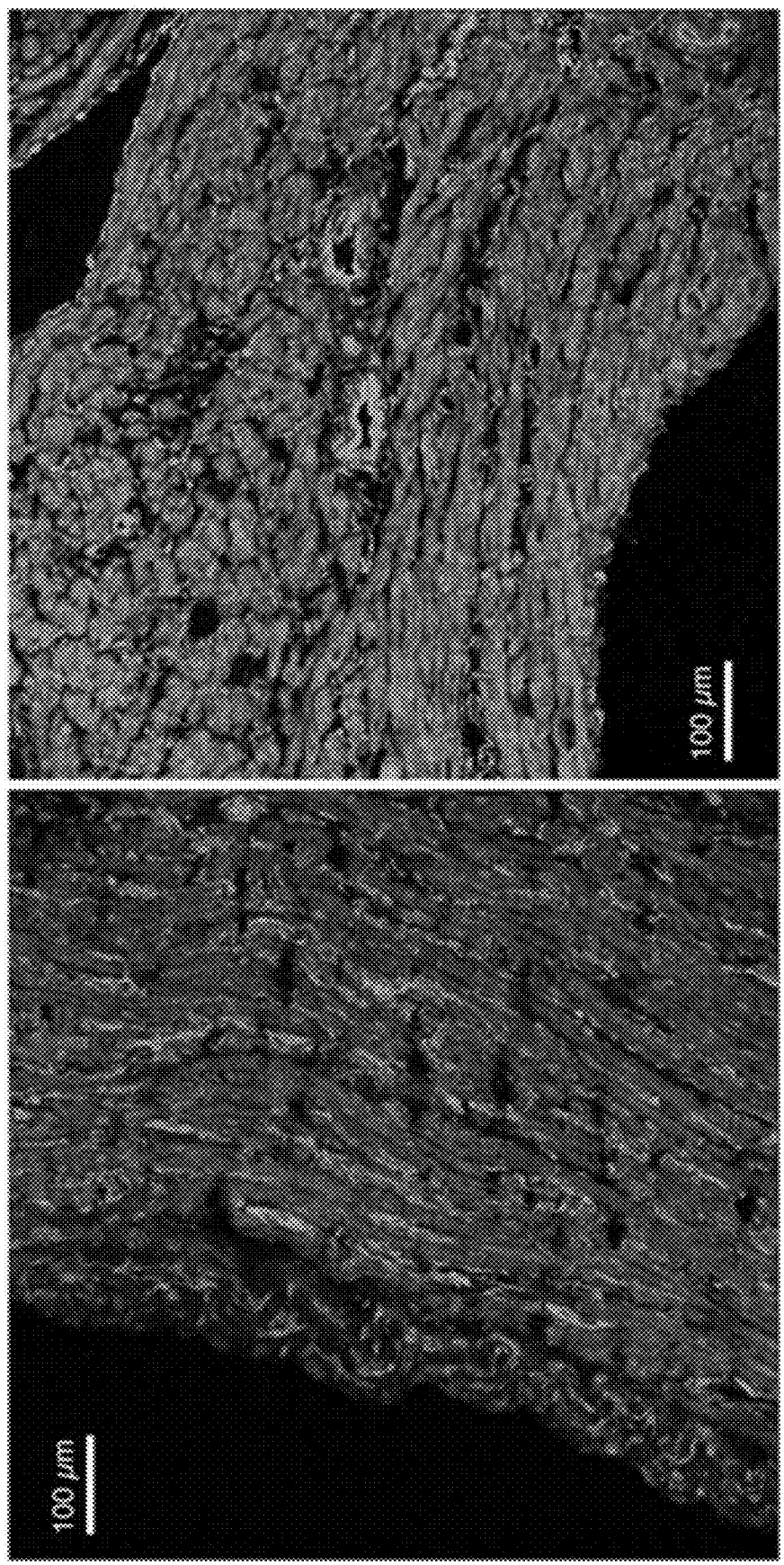
FIG. 1 is two immunofluorescence images using antiserum against ox-CaMKII in fixed sections of right atrial tissue from patients with sinus rhythm (SR) (left image) or AF (right image).

The present invention will be understood by reference to the following detailed description, which should be read in conjunction with the appended drawings. It is to be appreciated that the following detailed description of various embodiments is by way of example only and is not meant to limit, in any way, the scope of the present invention. In the summary above, in the following detailed description, in the claims below, and in the accompanying drawings, reference is made to particular features (including method steps) of the present invention. It is to be understood that the disclosure of the invention in this specification includes all possible combinations of such particular features, not just those explicitly described. For example, where a particular feature is disclosed in the context of a particular aspect or embodiment of the invention or a particular claim, that feature can also be used, to the extent possible, in combination with and/or in the context of other particular aspects and embodiments of the invention, and in the invention generally. The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40% means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm. The embodiments set forth the below represent the necessary information to enable those skilled in the art to practice the invention and illustrate the best mode of practicing the invention. In addition, the invention does not require that all the advantageous features and all the advantages need to be incorporated into every embodiment of the invention.

Turning now to FIGS. 1A through 36B, a brief description concerning the various components of the present invention will now be briefly discussed.

Oxidative stress has been associated with AF but the exact mechanisms and downstream signaling has remained unclear. Hydrogen sulfide and Nitric oxide are two gasotransmitters in the human body. These two gasotransmitters play a role in the pathogenesis of heart diseases, especially atherosclerosis and heart failure but their role in cardiac arrhythmias, especially AF had not yet been explored by the inventors. Hydrogen sulfide and nitric oxide modify the redox state of the cardiovascular system. Reduced hydrogen sulfide levels in a genetically modified mice, where the gene for the enzyme Cytathionine γ-Lyase (CSE), which generates hydrogen sulfide is knocked out, is associated with increased reactive oxygen species in the ventricle of the heart. The experiments in the inventors' lab show for the first time that superoxide levels are significantly elevated in the atria of these CSE knock out mice compared to wild type mice, a difference that is far more prominent than in the ventricles.

The inventors found that CSE knockout mice have a significantly higher incidence of inducible persistent AF, defined as any AF that lasts more than 90 seconds after induction. Atrial myocyte single cell patch clamping experiments showed that the action potential duration of atrial myocytes from the CSE knock out mice were significantly prolonged compared to the wild type atrial myocytes, evidencing a mechanism for increased susceptibility to AF in these mice. The inventors observed that female CSE knockout mice had exaggerated differences with their wild type counterparts with regards to inducible persistent AF incidence compared to male CSE knockout mice. When the inventors administered diallyl trisulfide (DATS; 200 ug/kg) retro-orbitally (i.e. I.V.) for three days to CSE knock out male mice, the risk of inducible persistent AF was reduced to near wild type levels, but there was no noticeable risk reduction of inducible persistent AF in the female CSE knock out mice.

CSE knockout female mice have levels of homocysteine, an α-amino-acid homologue of Cysteine, that is 3-4 fold increased compared to male CSE knockout mice. Homocysteine induced reactive oxygen species reduces the ability of eNOS to properly function in generating nitric oxide (NO). To explain the differences that the inventors observed between male and female CSE knockout mice in their response to DATS, the inventors measured NO levels in the atrium of CSE knock out male and female mice and compared them to their wild type counterparts. While the NO levels in male CSE KO mice were comparable to male wild type mice, the levels were markedly decreased in female CSE mice compared to female wild type mice. Based on this observation, the inventors tested if augmentation of NO bioavailability to female CSE knockout mice would reverse the female CSE knockout mice's susceptibility to inducible persistent AF. The inventors found that intraperitoneal administration of sodium nitrite (165 ug/kg) for 3 days did in fact decrease the incidence of inducible persistent AF.

The inventors' discovery that hydrogen sulfide and nitrite therapy can reduce the incidence of inducible AF has significant ramifications. The strongest risk factors for AF, namely hypertension, diabetes, advanced age, and heart failure are all associated with decreased levels of hydrogen sulfide similar to the CSE knock out mice. Furthermore, these conditions are also associated with decreased NO levels. Episodes of AF in these patients are triggered/induced by factors that increase sympathetic tone, inflammation and a reflex demand for increased heart rate. Post-operative state, sepsis/septic shock, hypovolemia and pain are some of the known triggers. Post-operative AF in particular increases morbidity, mortality, length of hospitalization and costs in patients with risk factors for AF. Previously, multiple interventions have been tried in this group of patients to prevent AF with mixed results at the best.

The inventors' experimental results evidence that administration of organic or inorganic forms of hydrogen sulfide and or nitrite orally, parenterally or locally to patients with risk factors for AF can prevent AF episodes, which then can prevent further remodeling of the atria that increase future episodes of AF. Additionally, administration of organic or inorganic forms of hydrogen sulfide and or nitrite orally, parenterally or locally to patients with AF can be therapeutic by reducing oxidative stress.

The inventors have invented a method of treating AF or a pre-AF condition in a mammal, preferably a human, comprising administering a therapeutically effective amount of one of organic or inorganic sulfide, organic or inorganic nitrite, both organic or inorganic sulfide and organic or inorganic nitrite, or pharmacologically acceptable salts, solvates, esters, amides, clathrates, stereoisomers, enantiomers, prodrugs or analogs thereof, or a combination thereof.

The inventors are aware that nitrate and sulfide levels may be therapeutically increased in the mammal to treat AF or a pre-AF condition through administration of prodrugs such as foods or compounds that cause an increase in nitrate and/or sulfide levels in the mammals. These alternative embodiments of the invention include administering beetroot juice (or extract), spinach, lettuce, arugula (rocket or rucola), bok choy, celery, chervil, collard greens, cress, radish, red beetroot, rhubarb, Swiss chard, basil, celeriac, Chinese cabbage, chard, coriander, endive, fennel, kohlrabi, leek, mustard greens, parsley, or any vegetable product to increase nitrate levels in mammal, and administering garlic, garlic extract, or cruciferous vegetables to increase sulfide levels in mammals. As another prodrug example, the inventors are aware that nitrate will convert to nitrite in the body. Therefore, in a further alternative embodiment of the invention, inorganic and/or organic nitrate may be administered in addition to or in place of nitrite to effectively administer nitrate to the mammal for the treatment of AF or pre-AF condition.

Nitrite has the chemical formula $NO_2^-$ and may exist as an ion in water. Sodium nitrite has the chemical formula $NaNO_2$ and typically dissolves in water to form the sodium ion $Na^+$ and the nitrite ion $NO_2^-$. It will further be understood that the present invention encompasses all such solvated forms (e.g., hydrates) of the nitrite compounds. In addition to sodium nitrite, representative inorganic nitrite compounds include: ammonium nitrite ($NH_4NO_2$), barium nitrite ($Ba(NO_2)_2$; e.g., anhydrous barium nitrite or barium nitrite monohydrate), calcium nitrite ($Ca(NO_2)_2$; e.g., anhydrous calcium nitrite or calcium nitrite monohydrate), cesium nitrite ($CsNO_2$), cobalt(II)nitrite ($Co(NO_2)_2$), cobalt (III)potassium nitrite ($CoK_3(NO_2)_6$; e.g., cobalt(III)potassium nitrite sesquihydrate), lithium nitrite ($LiNO_2$; e.g., anhydrous lithium nitrite or lithium nitrite monohydrate), magnesium nitrite ($MgNO_2$; e.g., magnesium nitrite trihydrate), potassium nitrite ($KNO_2$), rubidium nitrite ($RbNO_2$), silver(I)nitrite ($AgNO_2$), strontium nitrite ($Sr(NO_2)_2$), and zinc nitrite ($Zn(NO_2)_2$).

Nitric oxide (NO) and hydrogen sulfide (H2S) are both produced endogenously via enzymes. NO is synthesized by neuronal NO synthase (nNOS), inducible NO synthase (iNOS), and endothelial NO synthase (eNOS). H2S is synthesized via the actions of cystathionine β-synthase (CBS), cystathionine γ-lyase (CSE or CGL), and 3-mercaptopyruvate sulfur transferase (3-MST). These gaseous molecules are produced in low concentrations ranging from low µmol/L to low µmol/L and are labile.

Figure 2A:
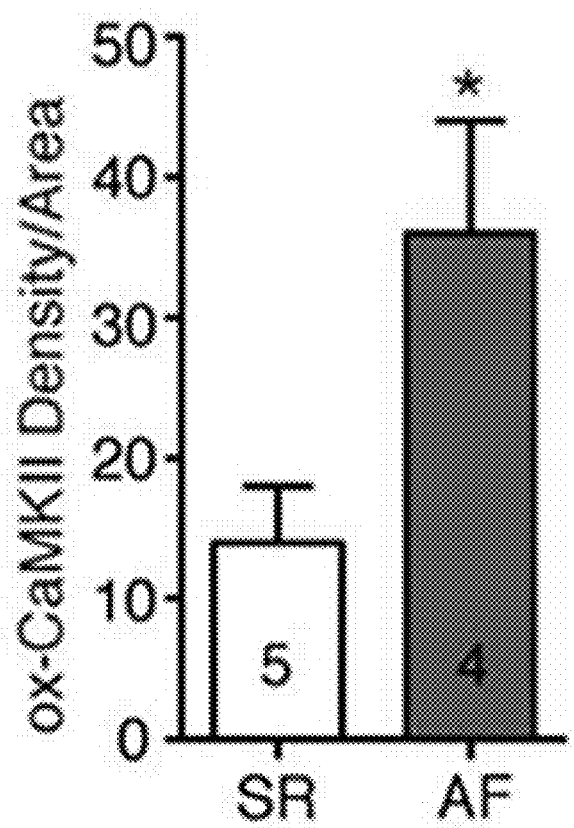
FIGS. 2A and 2B are bar graphs sowing ox-CaMKII density/area for SR and AF images from FIGS. 1 (2A), and showing percent mice with AF of four subgroups of mice (2B).
Figure 2B:
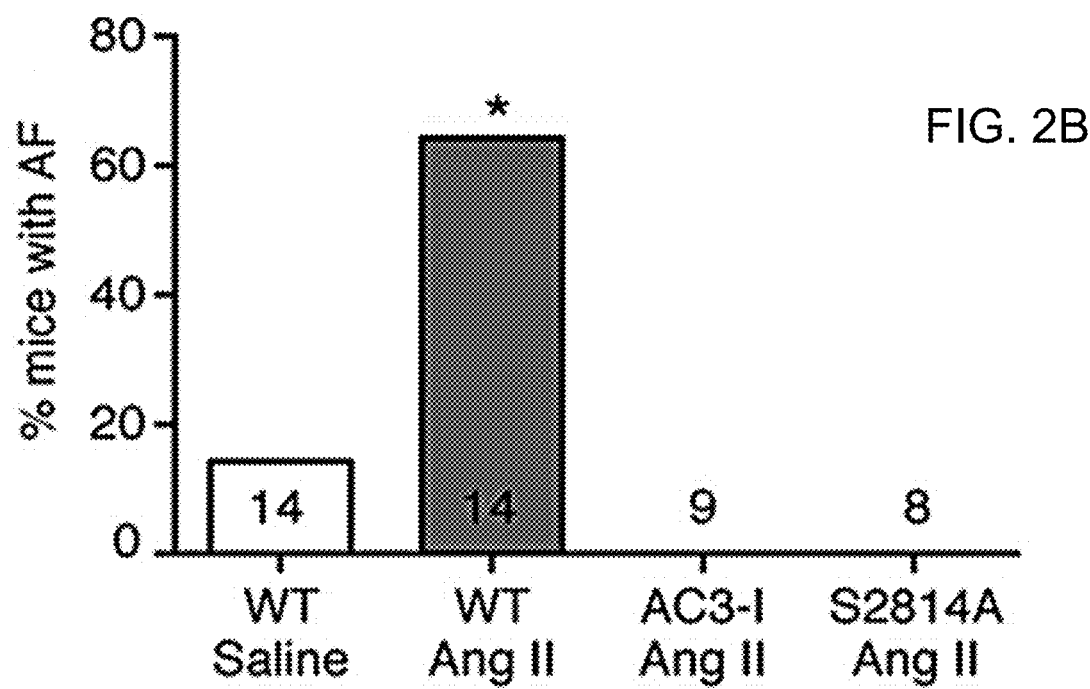

Turning now to FIGS. 1 to 2B, Oxidized $Ca^{2+}$/calmodulin-dependent protein kinase II (ox-CaMKII) was shown to be increased in atria from patients with atrial fibrillation (AF). Representative immunofluorescence images using antiserum against ox-CaMKII in fixed sections of right atrial tissue from patients with sinus rhythm (SR) or AF. Image quantification showed significantly higher ox-CaMKII in patients with AF compared with those with SR (*$P<0.05$, Student's t test). Representative immunoblots with ox-CaMKII antiserum in right atrial tissue homogenates from patients in SR or AF were made. Quantification of the immunoblots showed significantly higher ox-CaMKII expression in patients with AF compared with SR (*$P<0.05$, Student t test). The percent value indicates the mean ox-CaMKII/GAPDH ratio as normalized to the mean ox-CaMKII/GAPDH ratio in the SR group. Representative immunoblots with total CaMKII antiserum in right atrial tissue homogenates from patients in SR or AF were made. Quantification of immunoblots showed similar total CaMKII expression in patients with AF and SR ($P=0.3$, Student's t test), with the percent value indicating the mean CaMKII/GAPDH ratio as normalized to the mean CaMKII/GAPDH ratio in the SR group. The numbers in the bars in the graphs in the Figures indicate the sample size in each group.

Turning to FIGS. 3A to 4B, the inventors hypothesized that oxidative stress plays a role in the pathogenesis of AF. Indeed, the prevalence of AF increases with age as does oxidative stress. However, the mechanisms linking redox state to AF are not well understood. In this study the inventors identified a link between oxidative stress and aberrant intracellular Ca2+ release via the type 2 ryanodine receptor (RyR2) that promotes AF. The inventors showed that RyR2 is oxidized in the atria of patients with chronic AF compared with individuals in sinus rhythm. To dissect the molecular mechanism linking RyR2 oxidation to AF the inventors used two murine models harboring RyR2 mutations that cause intracellular Ca2+ leak. Mice with intracellular Ca2+ leak exhibited increased atrial RyR2 oxidation, mitochondrial dysfunction, reactive oxygen species (ROS) production and AF susceptibility. Both genetic inhibition of mitochondrial ROS production and pharmacological treatment of RyR2 leakage prevented AF. Collectively, the inventors' results indicate that alterations of RyR2 and mitochondrial ROS generation form a vicious cycle in the development of AF. The experimental results evidence that targeting this previously unrecognized mechanism will prevent and treat AF. As the results in FIGS. 3A-4B show, increased oxidation of the atrial RyR2 complex in patients with AF and in RyR2-S2808D+/+mice.

Turning to FIGS. 5A and 5B, H2S was found to be decreased in patients with heart failure. Circulating hydrogen sulfide levels are diminished in heart failure patients. The inventors evaluated H2S levels in heart failure patients (n=24) compared to age-matched control subjects (n=20). Serum free H2S (µM) levels were significantly reduced ($P<0.05$) in heart failure patients. Serum samples were obtained from patients enrolled in the Atlanta Cardiomyopathy Consortium (TACC). This prospective cohort study enrolls patients from the Emory University-affiliated teaching hospitals, the Emory University Hospital and Emory University Hospital Midtown, and Grady Memorial Hospital in Atlanta. All patients undergo detailed medical history surveys, electrocardiogram, standardized questionnaires, and blood and urine sample collection at baseline. All patients provide written informed consent prior to enrollment. The Emory University Institutional Review Board has approved this study. H2S levels were measured in the blood according to previously described methods.

Figure 6:
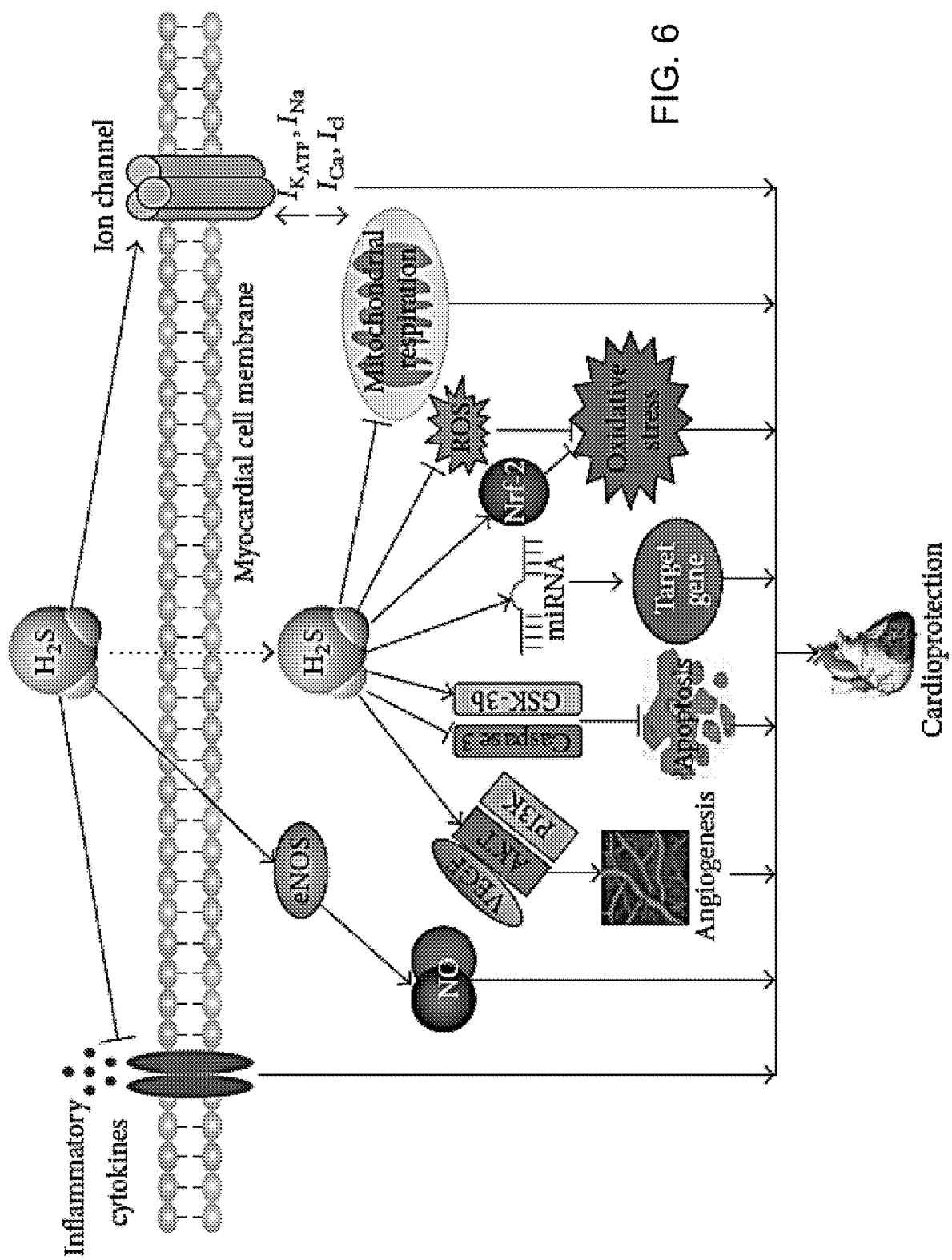
FIG. 6 is a schematic representation of various cardioprotective mechanisms of H2S.

Turning to FIG. 6, different signaling pathways activated by H2S showing the cardioprotective effects is shown. H2S can protect heart against diseases via different mechanisms: H2S prevents inflammatory response mediated by inflammatory cytokines. H2S stimulates angiogenesis by increasing the expression of VEGF and activating phosphatidylinositol 3-kinase (PI3K) and Akt. H2S activates endothelial nitric oxide synthase (eNOS) and augments NO bioavailability. H2S significantly protects against cardiomyocyte apoptosis by suppressing the activation of caspase-3 and upregulating the expression of glycogen synthase kinase-3 (GSK-3β). H2S plays its role by regulating the expression of miRNA. H2S also protects mitochondrial function via inhibition of mitochondrial respiration. H2S exerts antioxidative action by activating nuclear-factor-E2-related factor-2 (Nrf2) dependent pathway and scavenging of ROS. H2S opens KATP channels, increases Na+ channels (Nav) current, and inhibits L-type Ca2+ channels and chloride channels, to produce cardioprotective effects.

Figure 7:
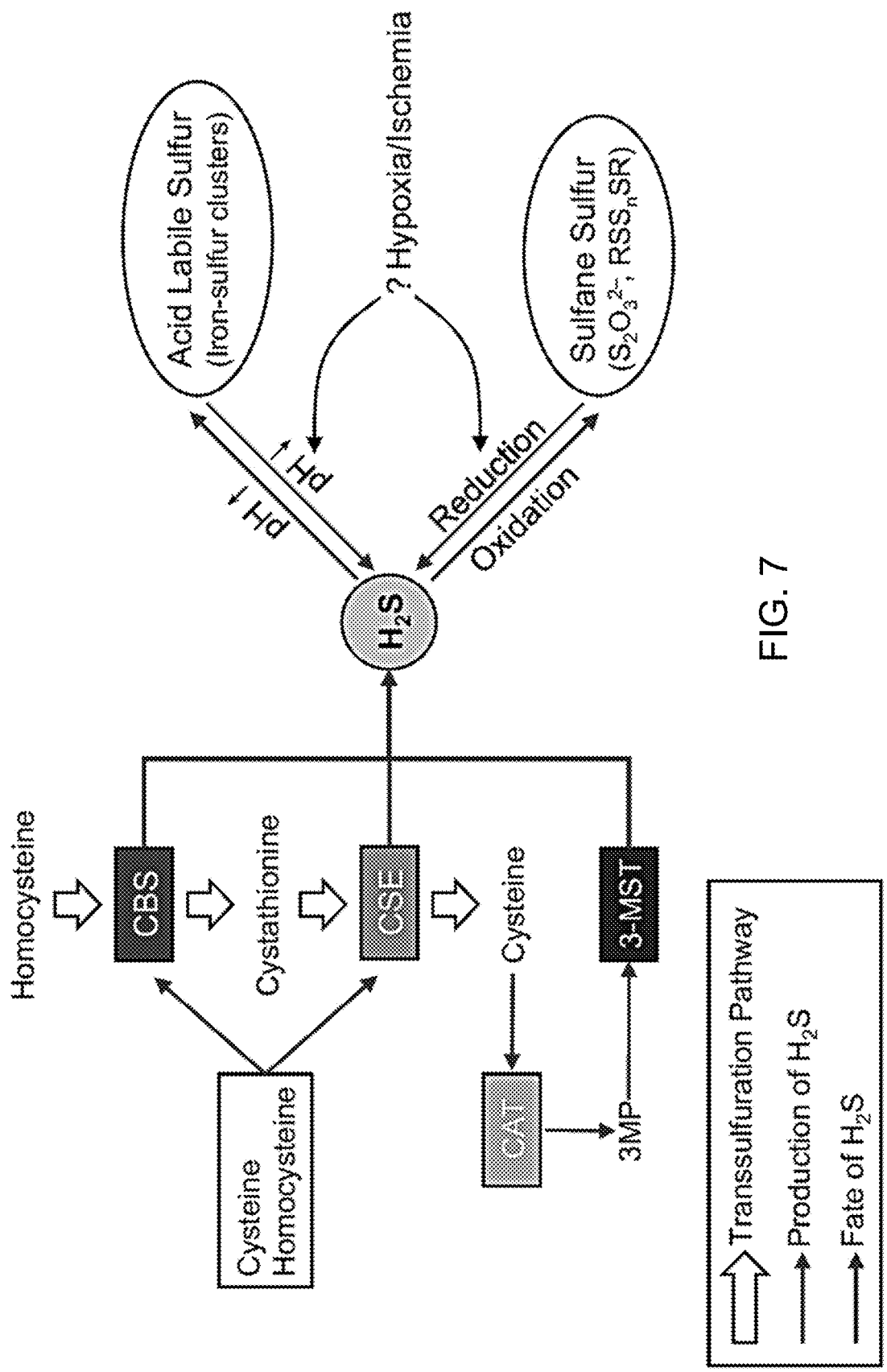
FIG. 7 is a schematic representation of biosynthesis pathways of endogenous H2S.
Figure 8A:
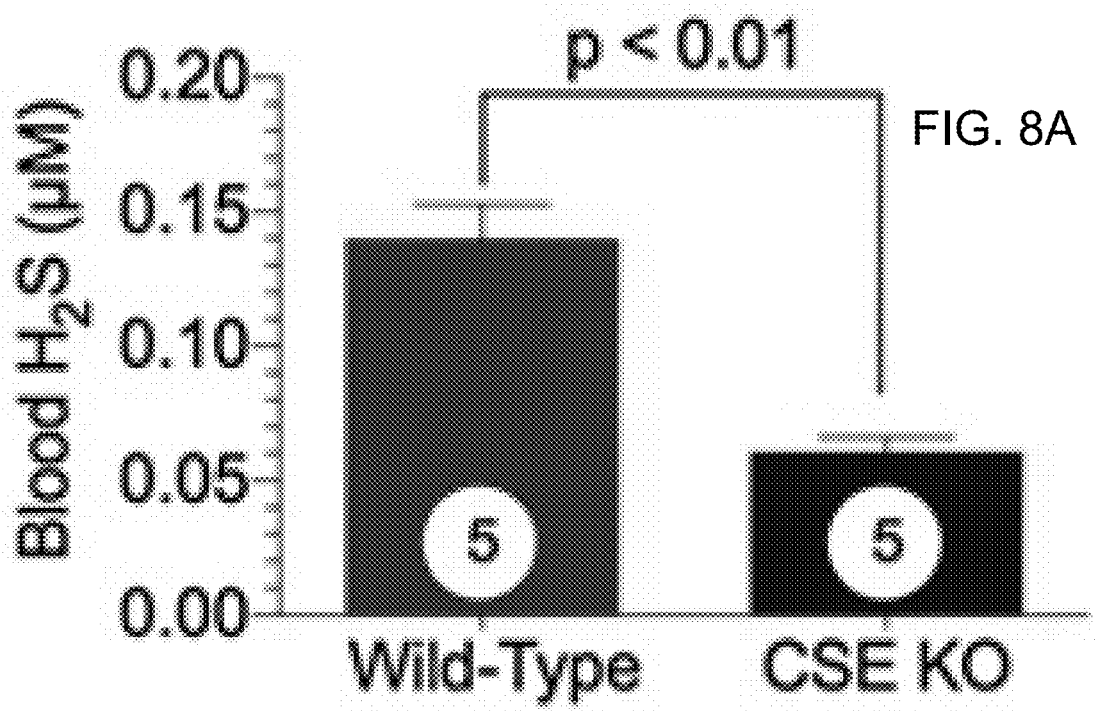
FIGS. 8A and 8B are bar graphs showing blood H2S (8A) and heart H2S (8B) for wild type and CSE KO mice.
Figure 8B:
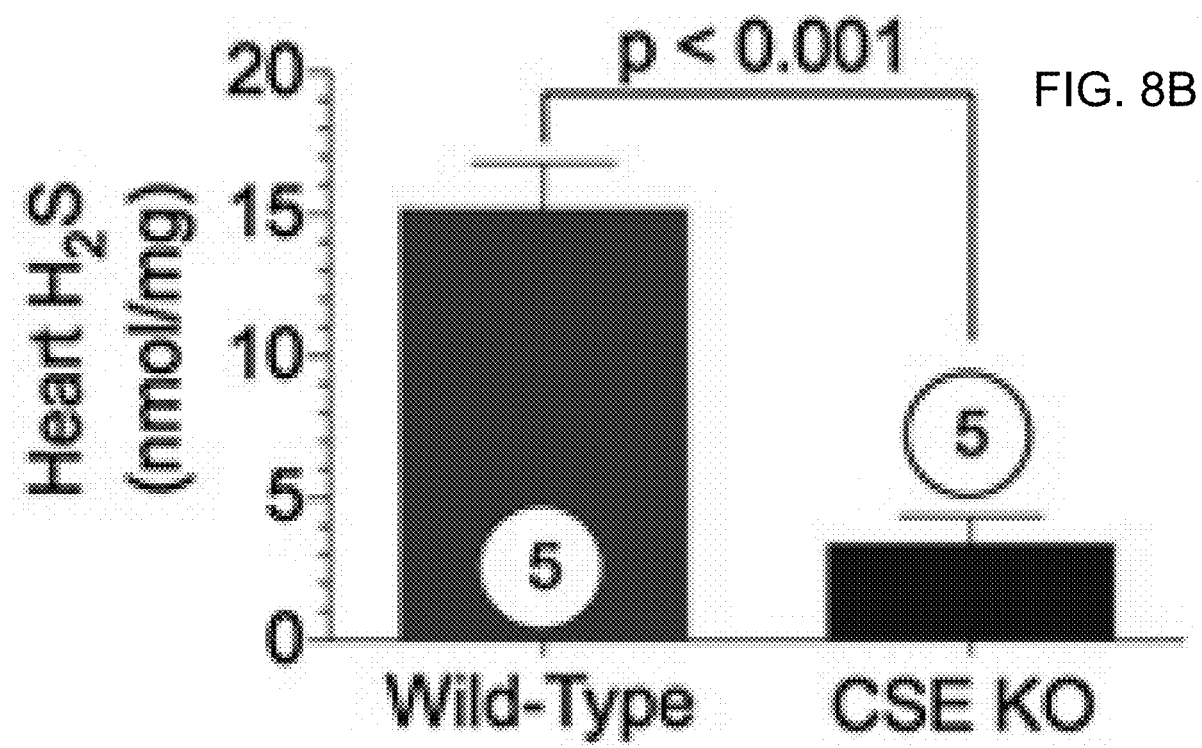

Turning to FIG. 7, Biosynthesis pathways of endogenous H2S is shown. Cystathionine-β-synthase (CBS) and cystathionine-γ-lyase (CSE) use L-cysteine as a substrate to produce H2S. However, 3-mercaptopyruvate sulfurtransferase (3-MST) uses 3-mercaptopyruvate (3-MP) as a substrate to form H2S. 3-MP is produced by cysteine aminotransferase (CAT) from L-cysteine in the presence of α-keto glutarate (α-KG); on the other hand, it is also produced by D-amino acid oxidase (DAO) from D-cysteine.

FIGS. 8A to 9B show that CSE Knock out (KO) causes decreased H2S and causes oxidative stress.

Turning to FIGS. 10A to 10D, it was found that CSE KO causes increase in atrial superoxide.

Figure 11:
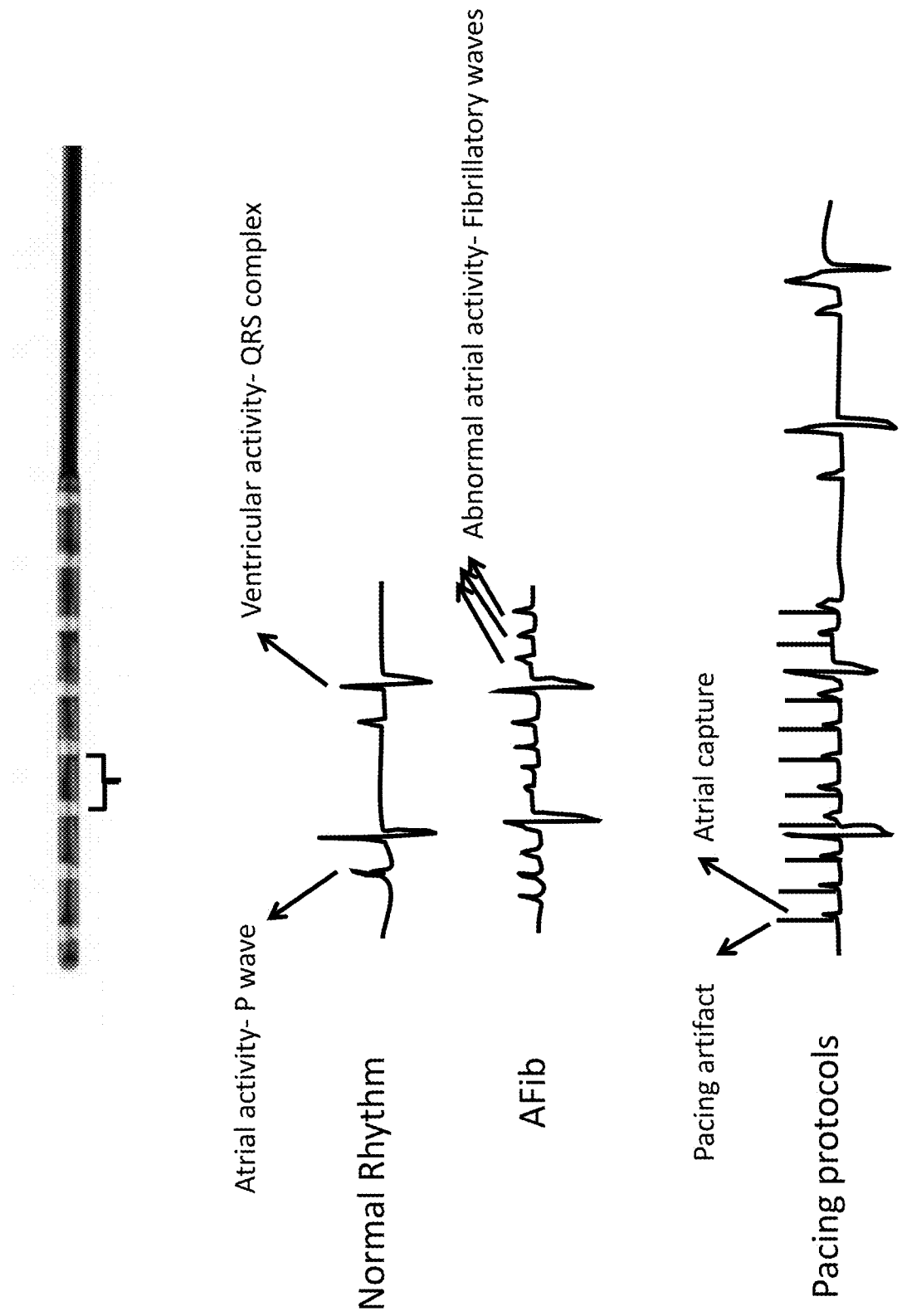
FIG. 11 is a schematic representation of mouse electrophysiology and AF induction in mice.
Figure 12A:
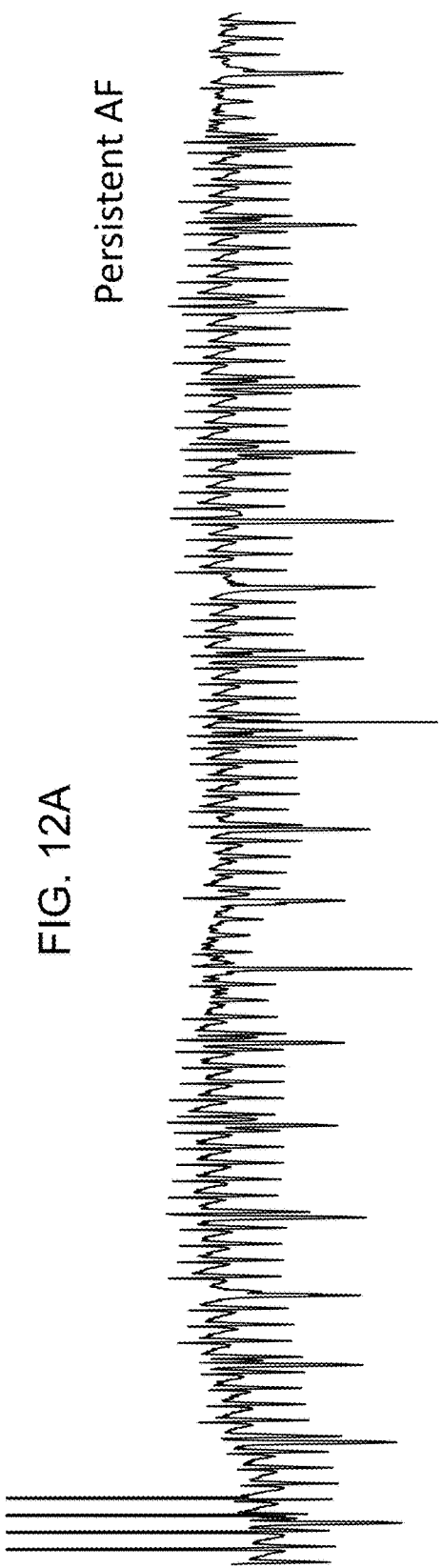
FIGS. 12A and 12B are electro cardio rhythms of persistent AF (12A) and non-persistent AF (12B).
Figure 12B:
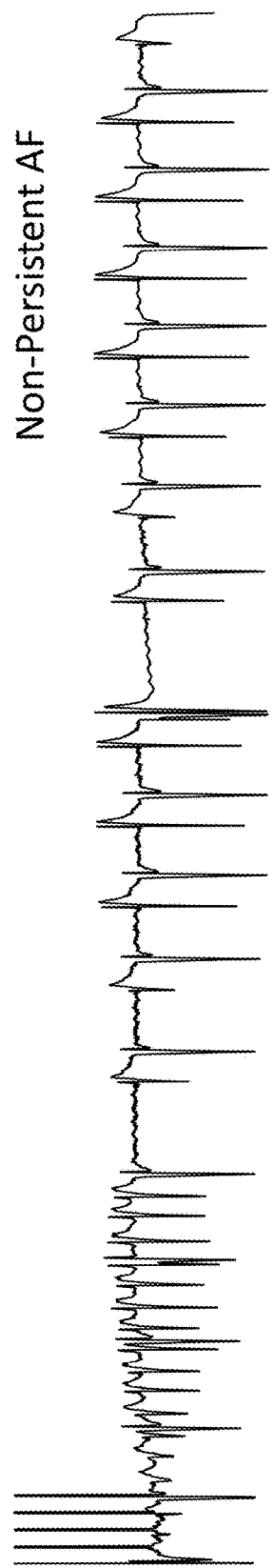

FIGS. 11 to 12B show mouse Mouse Electrophysiology and AF induction in mice and persistent AF and short run or non-persistent AF.

Figure 13:
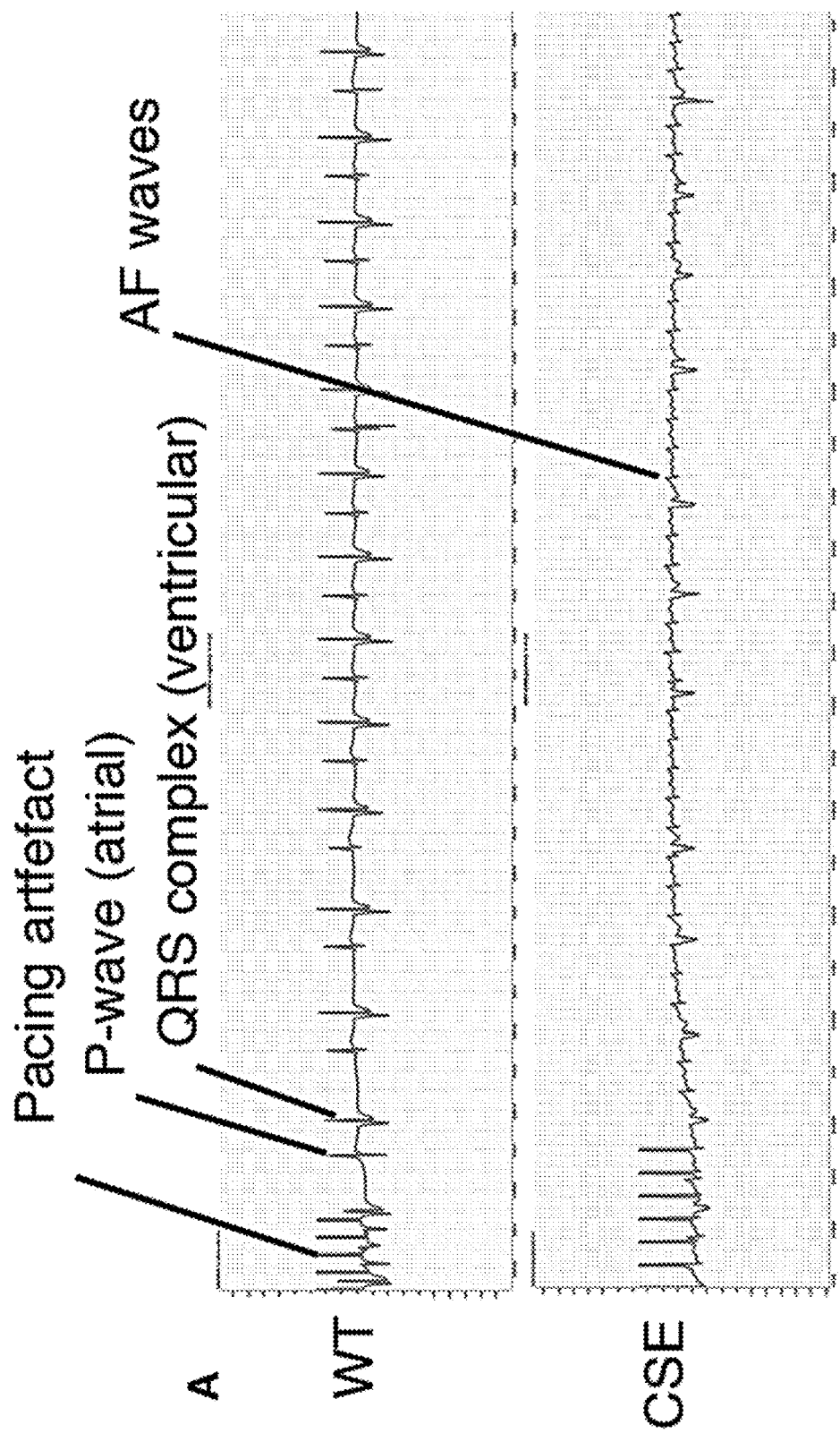
FIG. 13 shows electro cardio rhythms of WT and CSE KO mice.

Turning to FIG. 13, AF in CSE KO mice is shown, and compared to wild type mice cardiac rhythm.

Figure 14A:
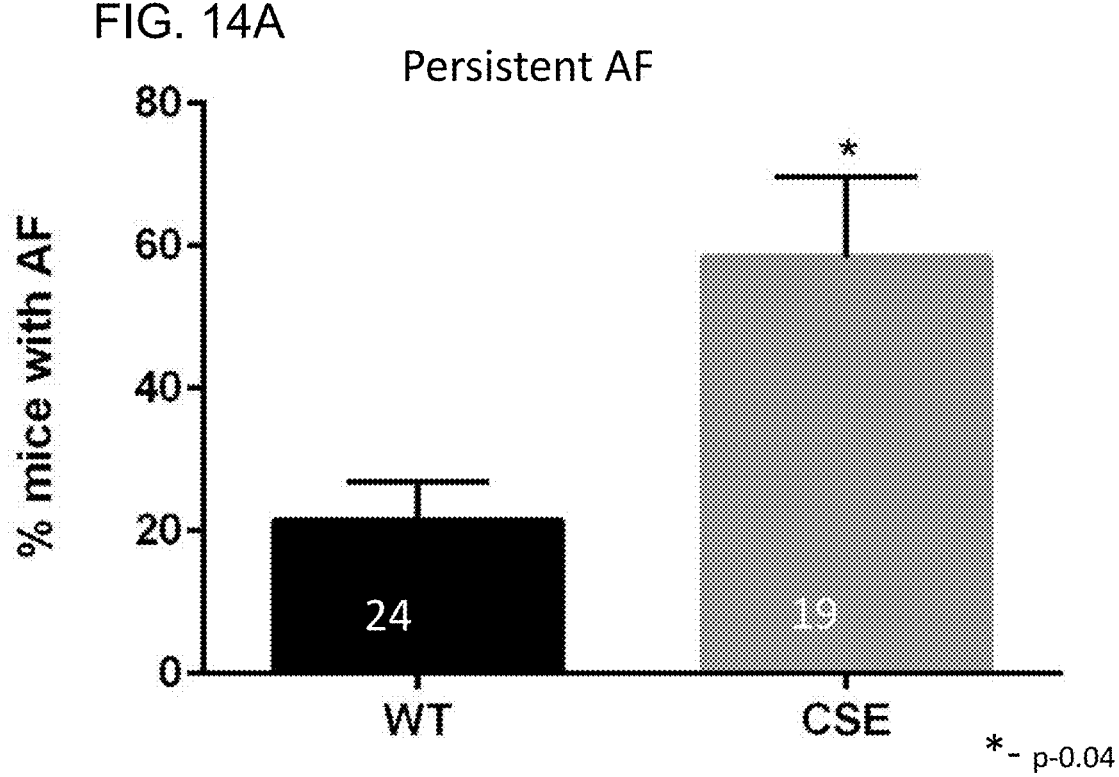
FIGS. 14A and 14B are bar graphs showing persistent AF (14A) and duration of any AF (14B) in WT and CSE KO mice.
Figure 14B:
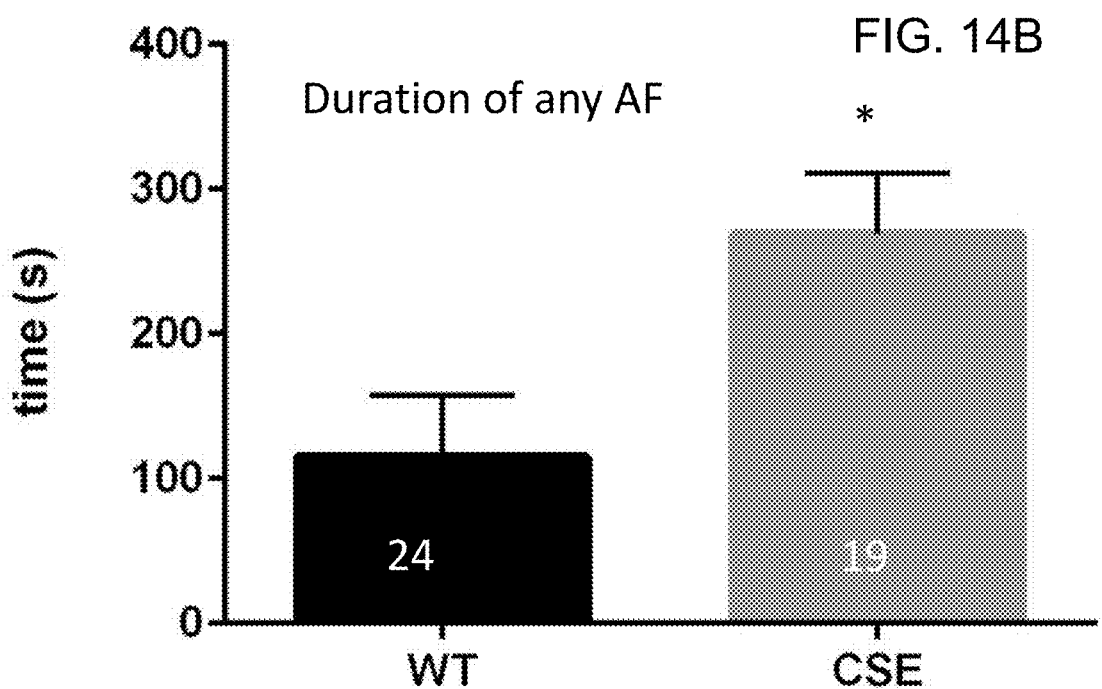

FIGS. 14A and 14B show incidence and duration of AF is increased in CSE KO mice compared to WT mice.

Figure 15:
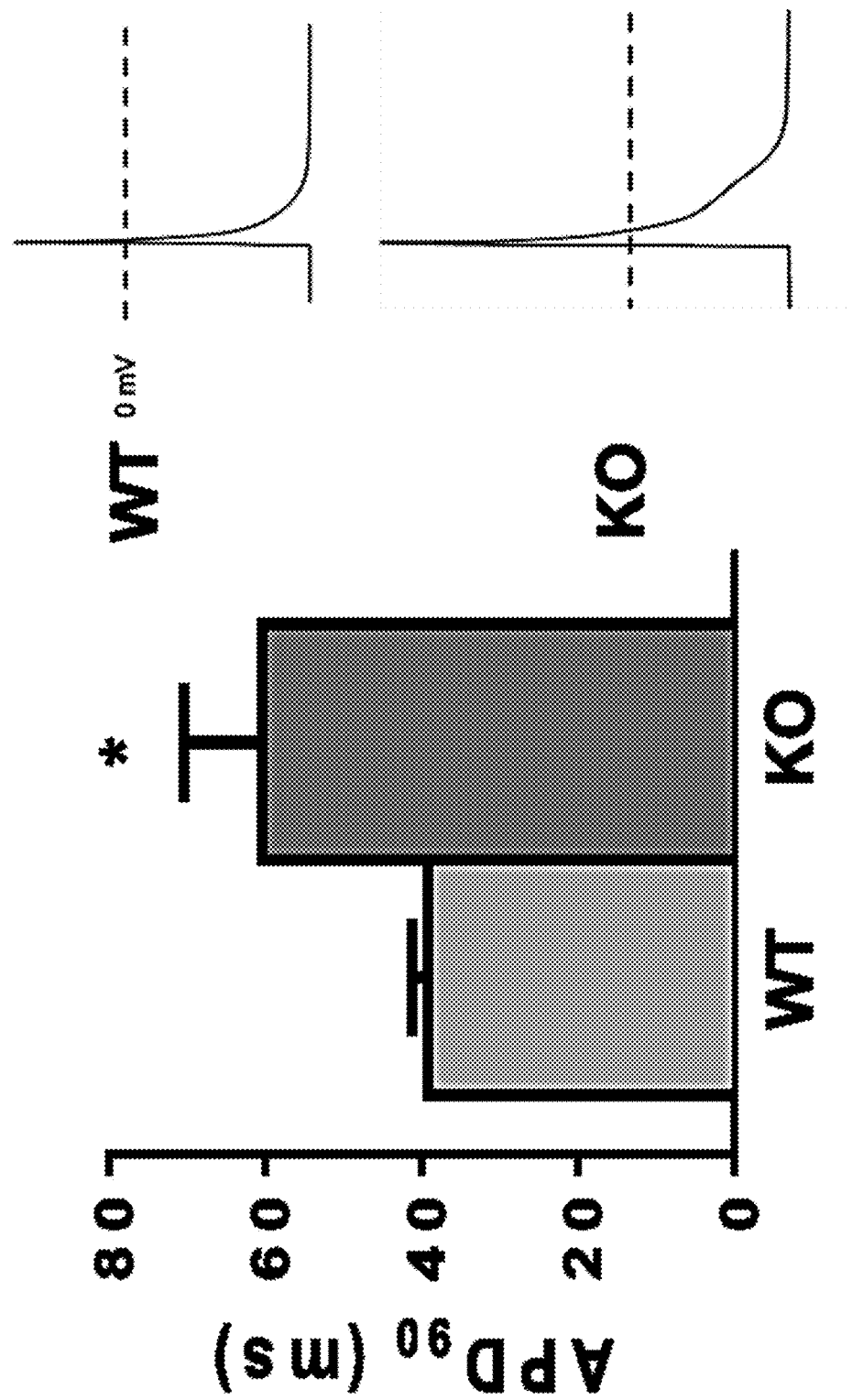
FIG. 15 is a bar graph and cardio waves showing atrial action potential duration of WT to CSE KO mice
Figure 16A:
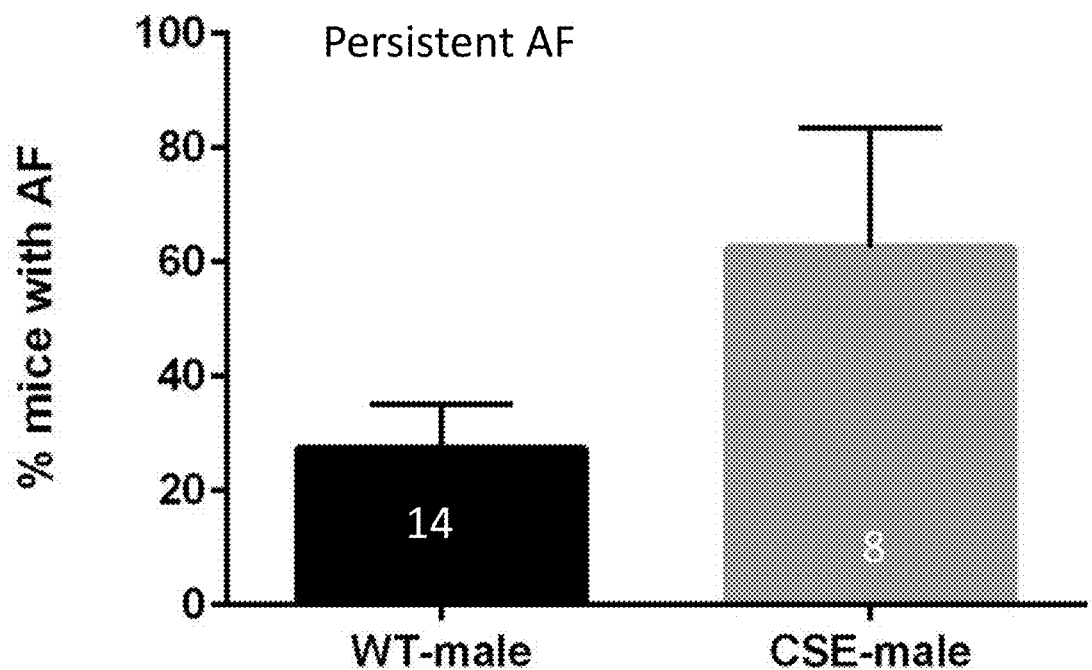
FIGS. 16A and 16B are bar graphs showing persistent AF (16A) and duration of any AF (16B) in WT male and CSE KO male mice.
Figure 16B:
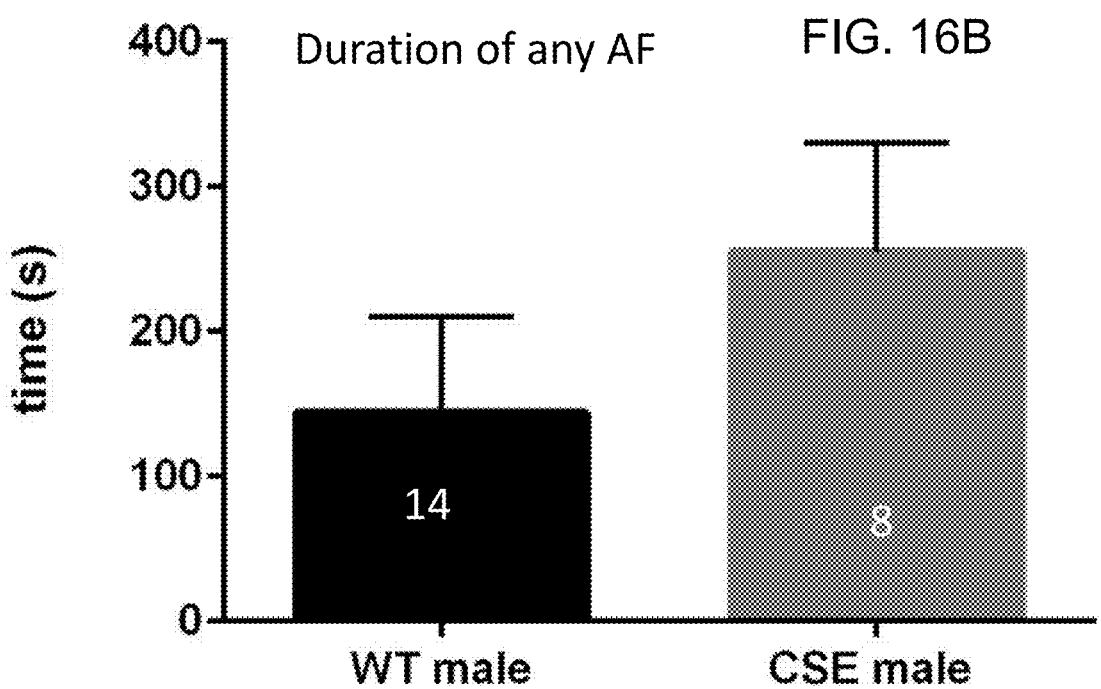
Figure 17A:
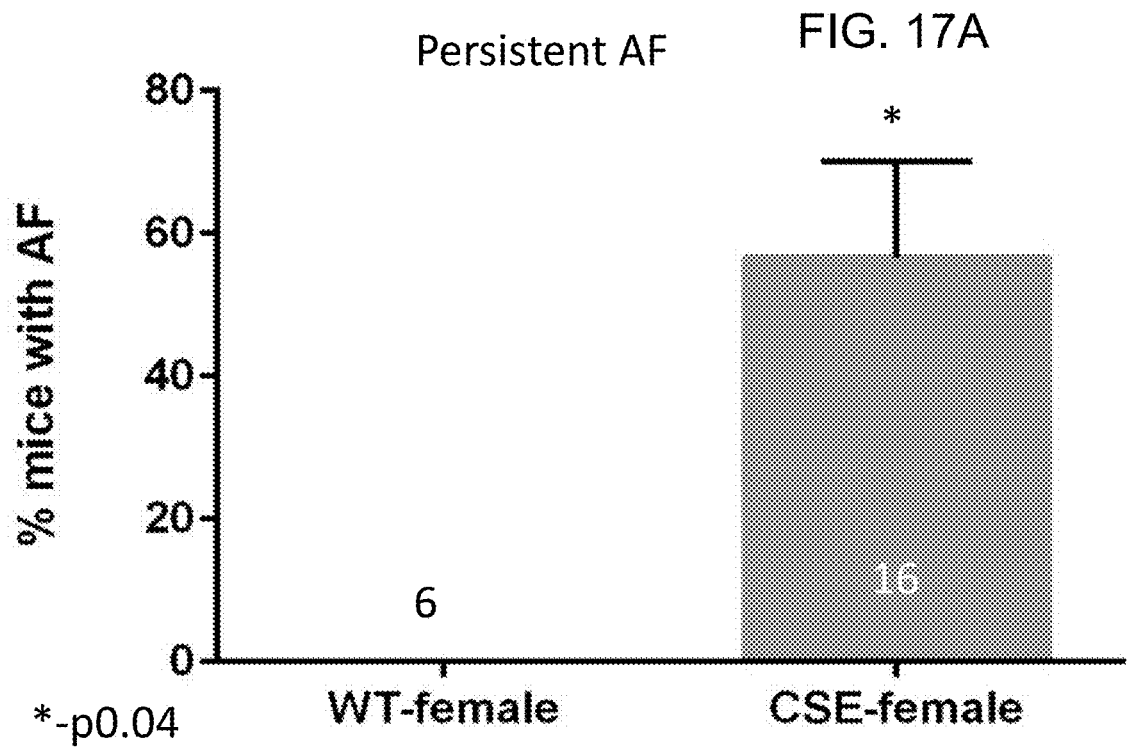
FIGS. 17A and 17B are bar graphs showing persistent AF (17A) and duration of any AF (17B) in WT female and CSE KO female mice.
Figure 17B:
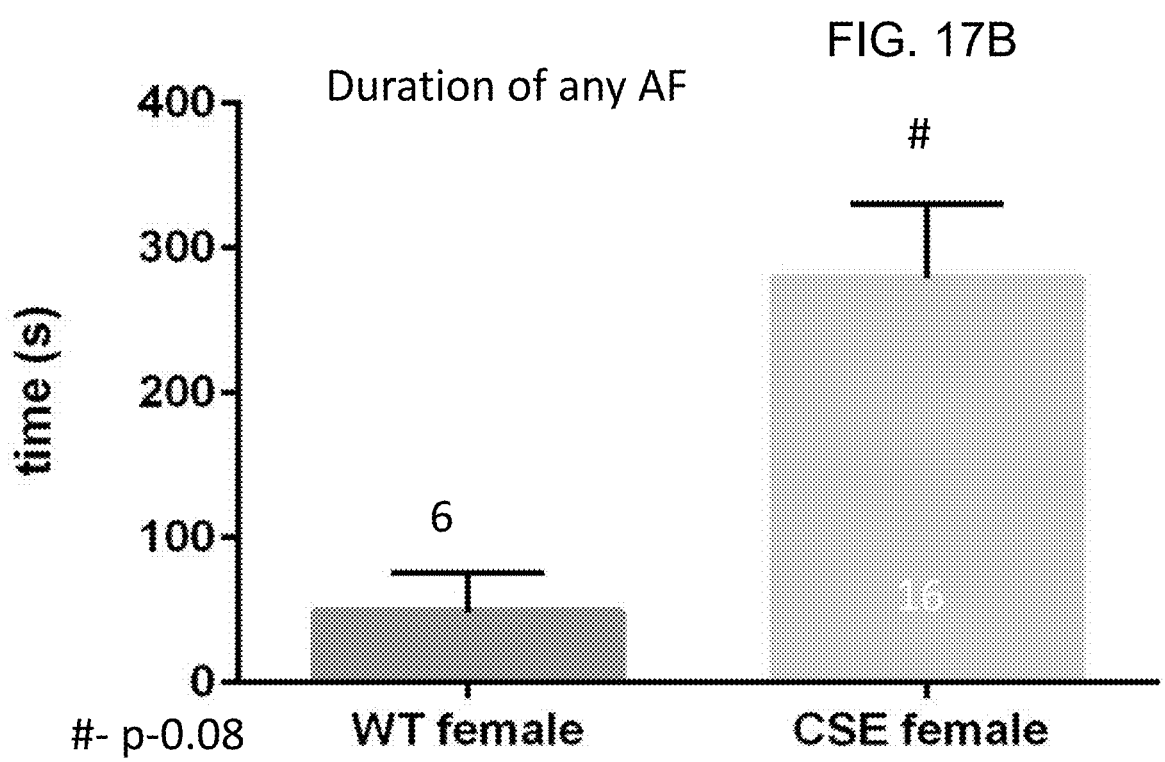

FIG. 15 shows that CSE KO mice have increased atrial action potential duration.

FIGS. 16A to 17B display gender variation in CSE KO mice for AF in persistent AF and duration of any AF.

Figure 18A:
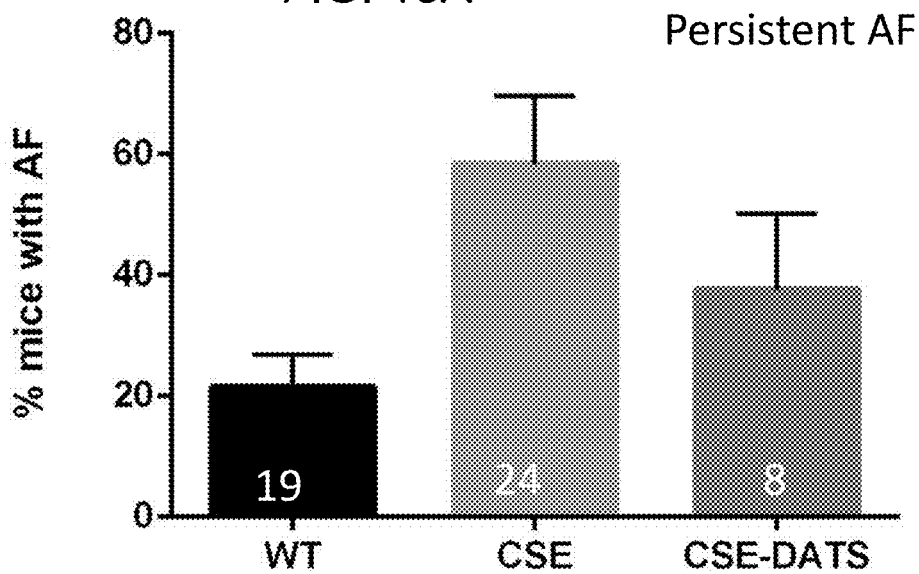
FIGS. 18A and 18B are bar graphs showing persistent AF (18A) and duration of any AF (18B) in WT, CSE KO, and CSE KO DATS treated mice.
Figure 18B:
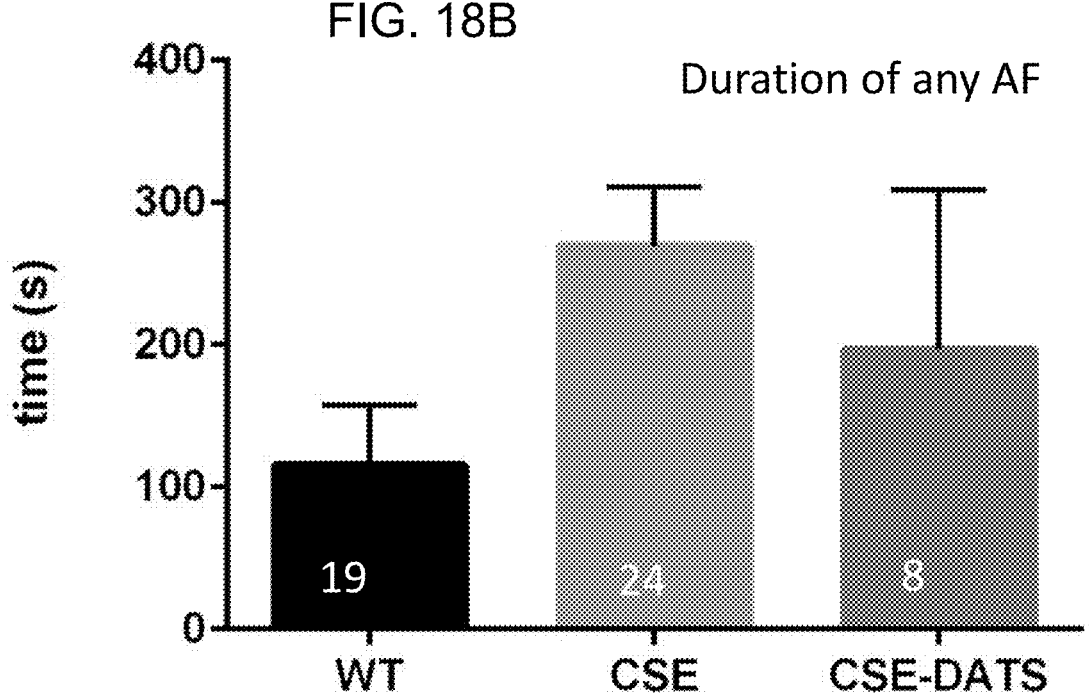
Figure 19A:
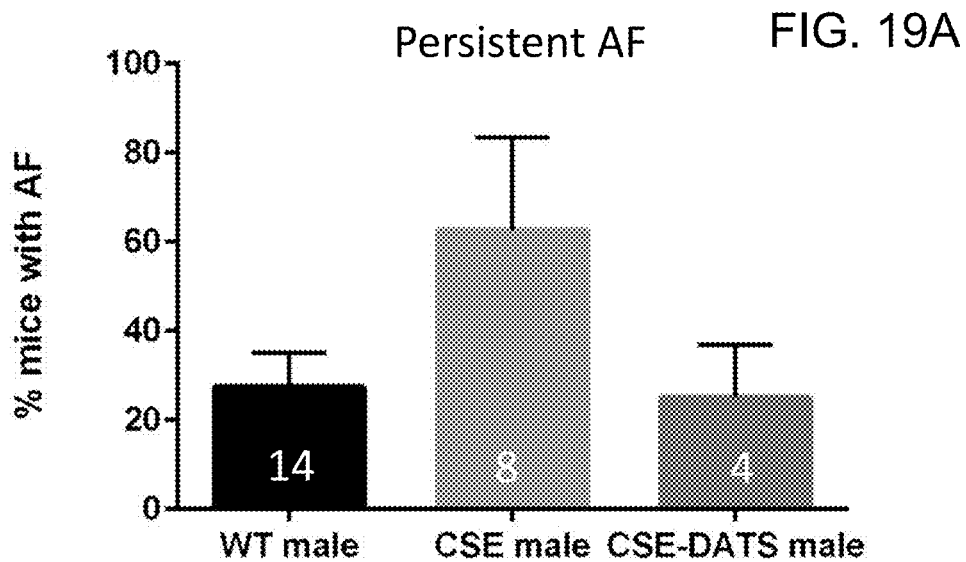
FIGS. 19A and 19B are bar graphs showing persistent AF (19A) and duration of any AF (19B) in WT male, CSE KO male, and CSE KO DATS treated male mice.
Figure 19B:
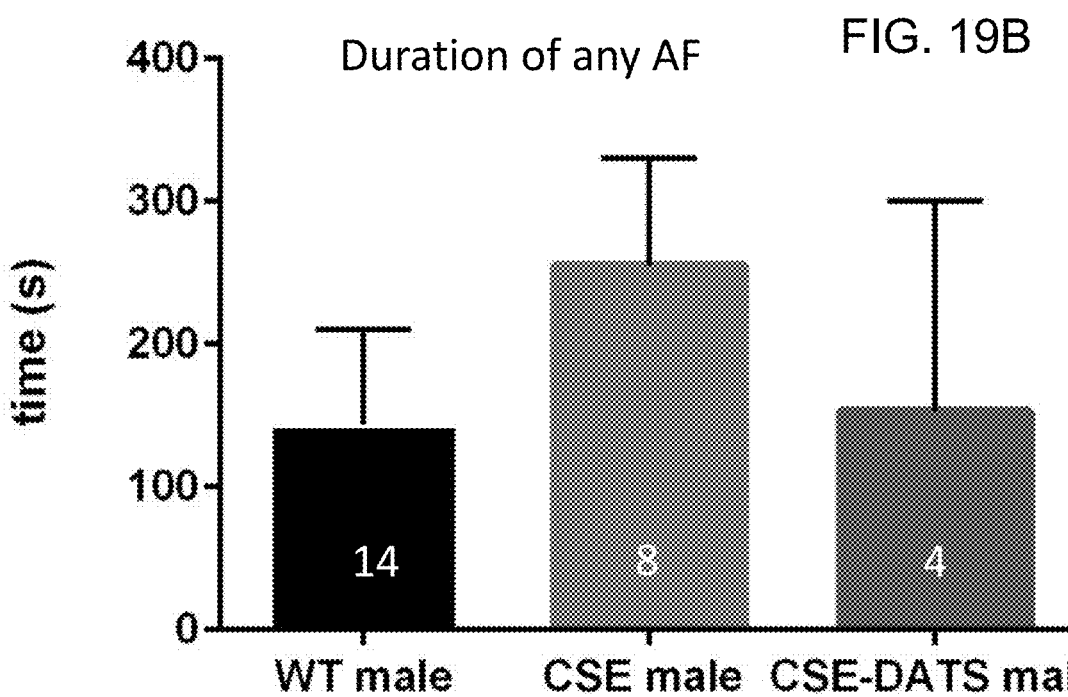
Figure 20A:
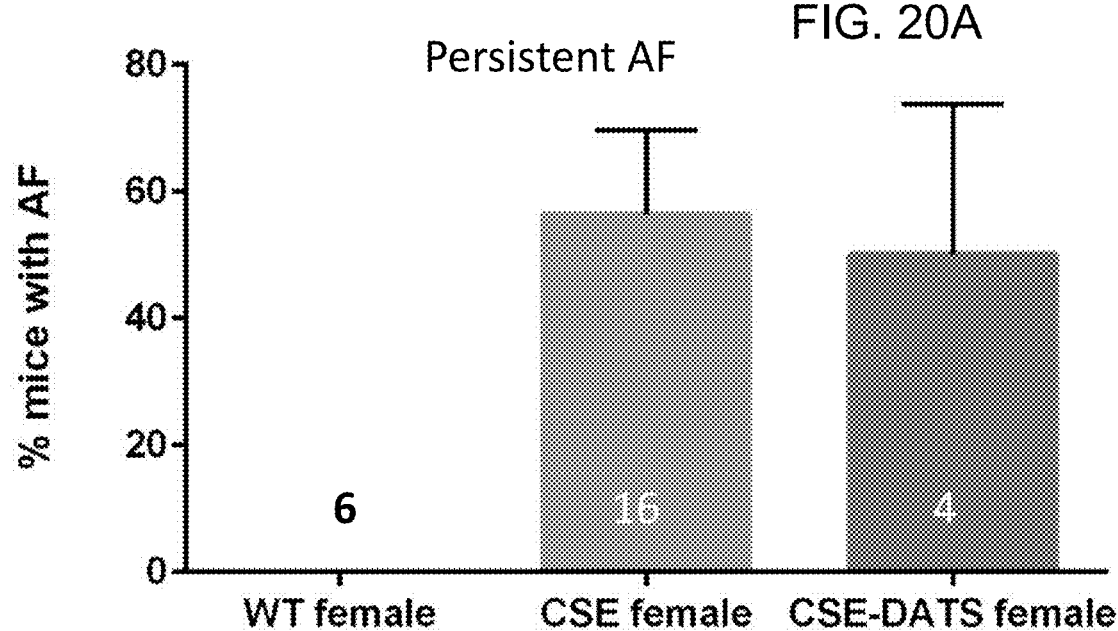
FIGS. 20A and 20B are bar graphs showing persistent AF (20A) and duration of any AF (20B) in WT female, CSE KO female, and CSE KO DATS treated female mice.
Figure 20B:
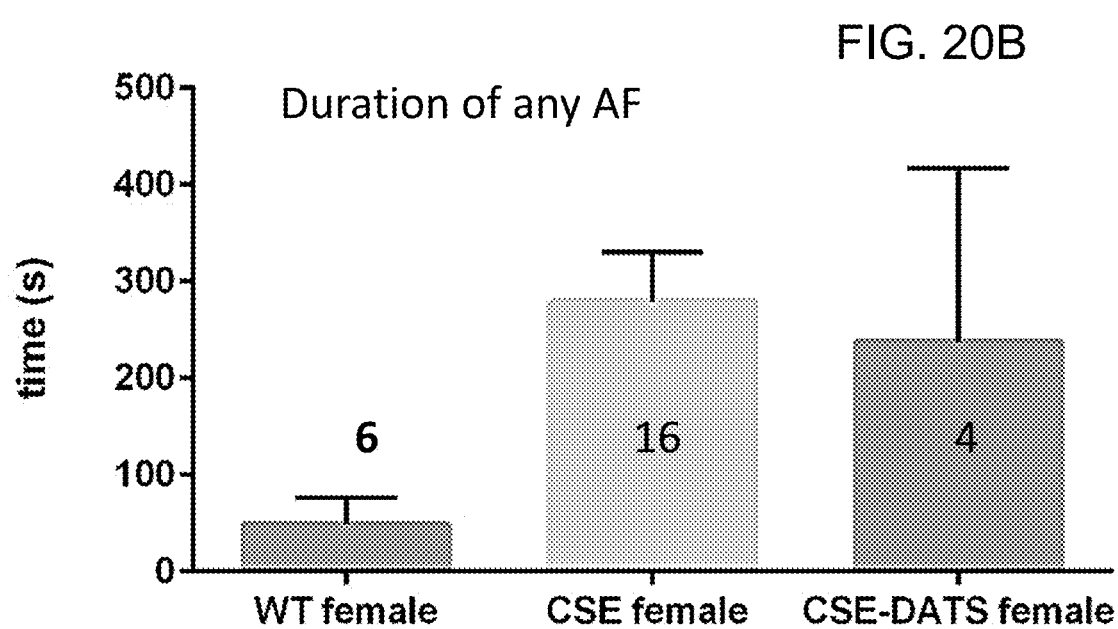

Turning to FIGS. 18A and 18B, DATS treatment and AF burden are shown. FIGS. 19A to 20B show Gender variations in response to DATS for CSE KO mice and AF.

Figure 21A:
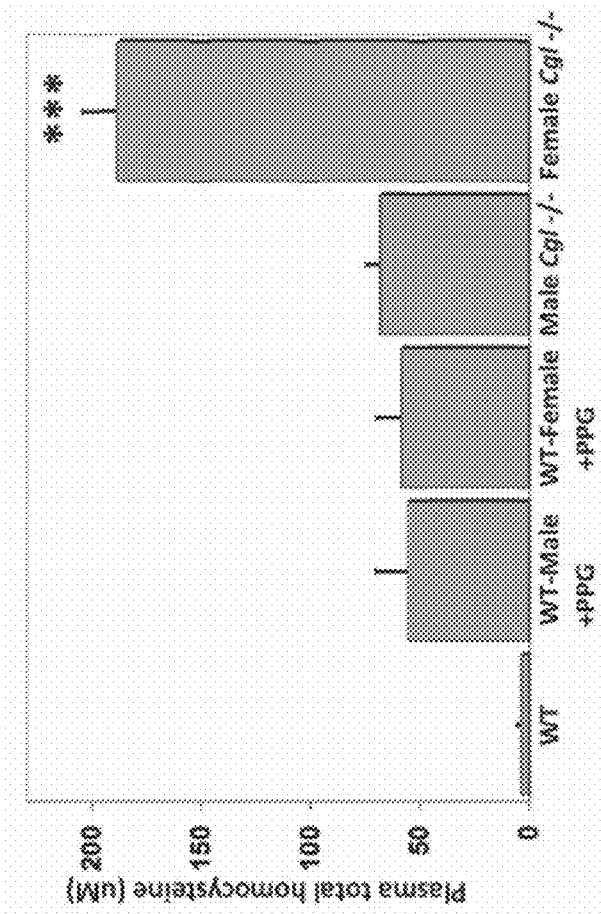
FIGS. 21A and 21B are a schematic representation of hyperhomocystenemia mechanism (21A) and a bar graph of plasma total homocysteine for various groups of mice (21B).
Figure 21B:
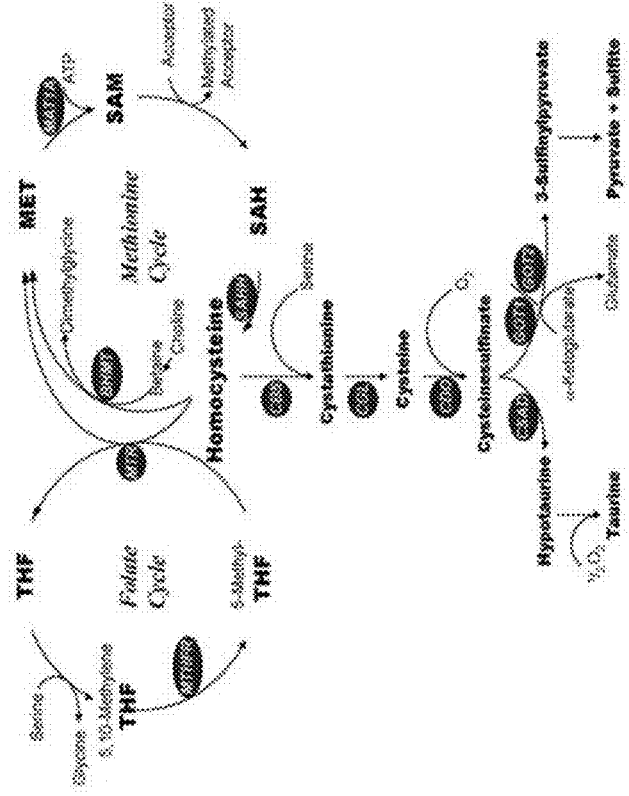

Turning to FIGS. 21A and 21B, female CSE KO mice are shown to have sever hyperhomocysenemia. In addition to its role in the endogenous synthesis of cysteine, cystathionine gamma-lyase (CGL) is a major physiological source of the vasorelaxant hydrogen sulfide. Cgl null mice are potentially useful for studying the influence of this compound upon vascular tone and endothelial function. Here, the inventors show that female Cgl null mice exhibit an approximate 45-fold increase in plasma total homocysteine compared to wild type controls. This level of homocysteine is approximately 3.5-fold higher than that observed in male Cgl null mice and is essentially equivalent to that observed in mouse models of cystathionine beta synthase deficient homocystinuria. Cgl null mice of both sexes exhibited decreased expression of methylenetetrahydrofolate reductase and cysteine sulfinate decarboxylase compared to WT controls. Female Cgl null mice exhibited a sex-specific induction of betaine homocysteine S-methyltransferase and methionine adenosyltransferase 1, alpha and a 70% decrease in methionine synthase expression accompanied by significantly decreased plasma methionine. Decreased plasma cysteine levels in female Cgl null mice were associated with sex specific dysregulation of cysteine dioxygenase expression. Comparative histological assessment between cystathionine beta-synthase and Cgl null mice indicated that the therapeutic potential of cystathionine against liver injury merits possible further investigation. Collectively, the inventors' data demonstrates the importance of considering sex when investigating mouse models of inborn errors of metabolism and indicate that while female Cgl null mice may be of questionable utility for studying the physiological role of hydrogen sulfide, they could serve as a useful model for studying the consequences of methionine synthase deficiency and the methylfolate trap.

Figure 22:
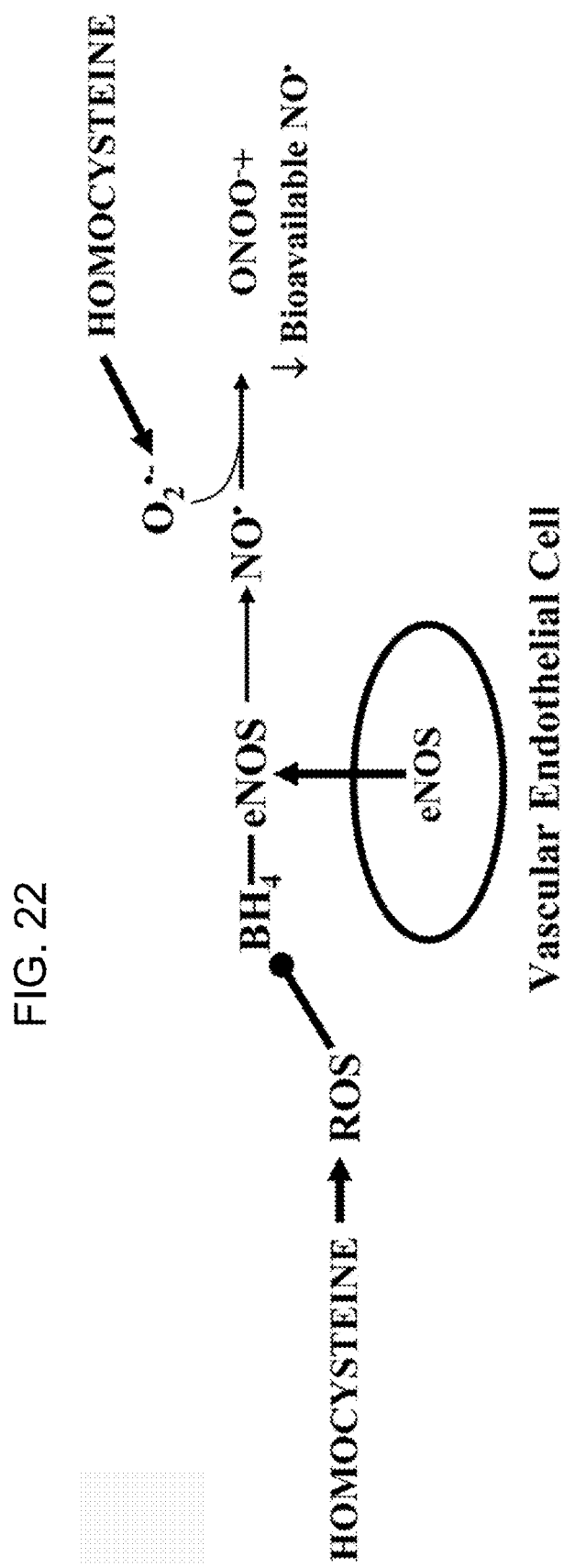
FIG. 22 is schematic representation of a mechanism by which homocysteine induced ROS decreases levels of bioavailable NO.

Tuning to FIG. 22, homocysteine-induced reactive oxygen species formation is shown to decrease levels of bioavailable NO. either by reducing the availability of key NOS cofactors, such astetrahydrobiopterin (BH4), or by inducing conversion of NO. to peroxynitrite (ONOO—). SOD, superoxide dismutase; eNOS, endothelial nitric oxide synthase.

Figure 23:
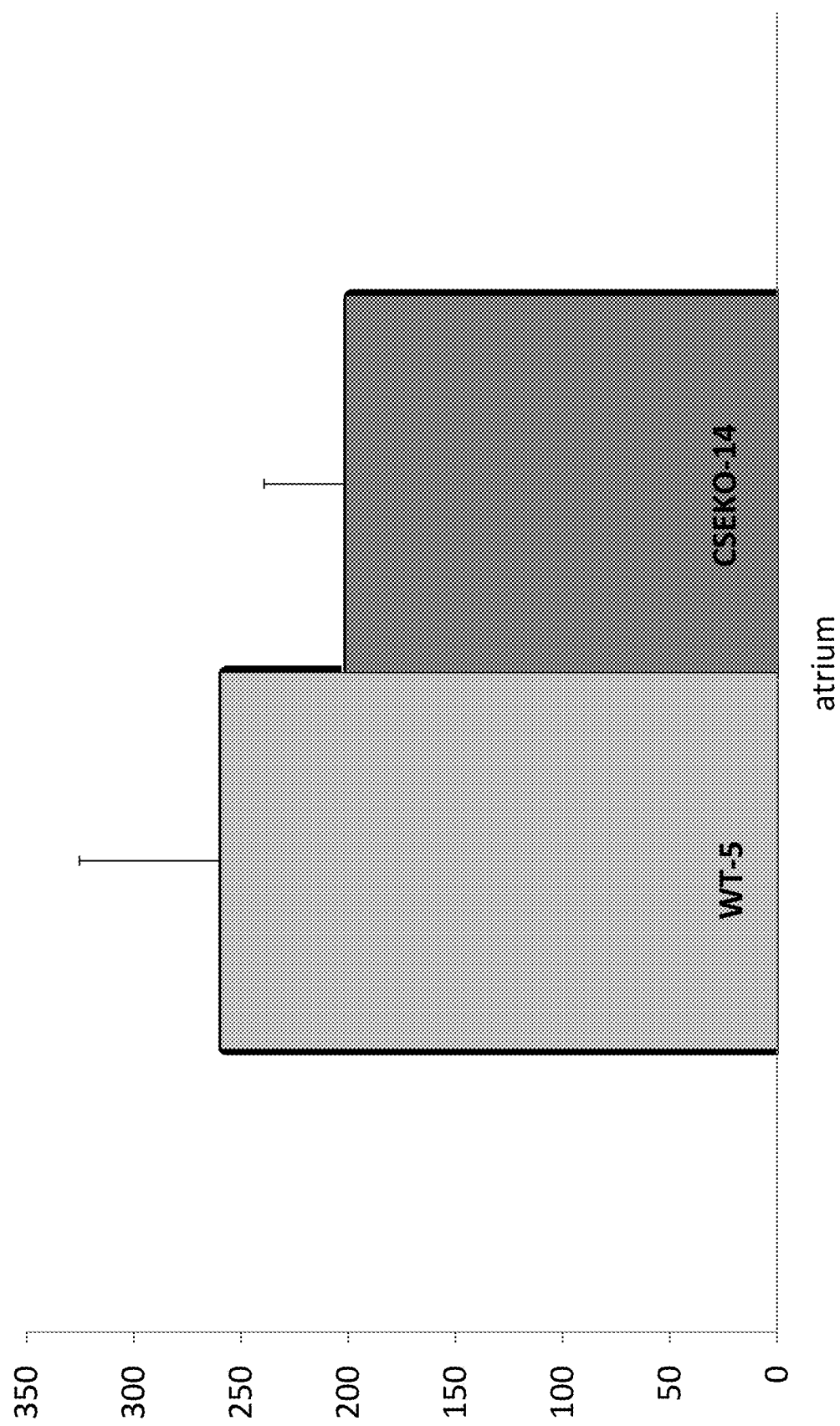
FIG. 23 is a bar graph showing NO levels in WT and CSE KO mice in atria.
Figure 24A:
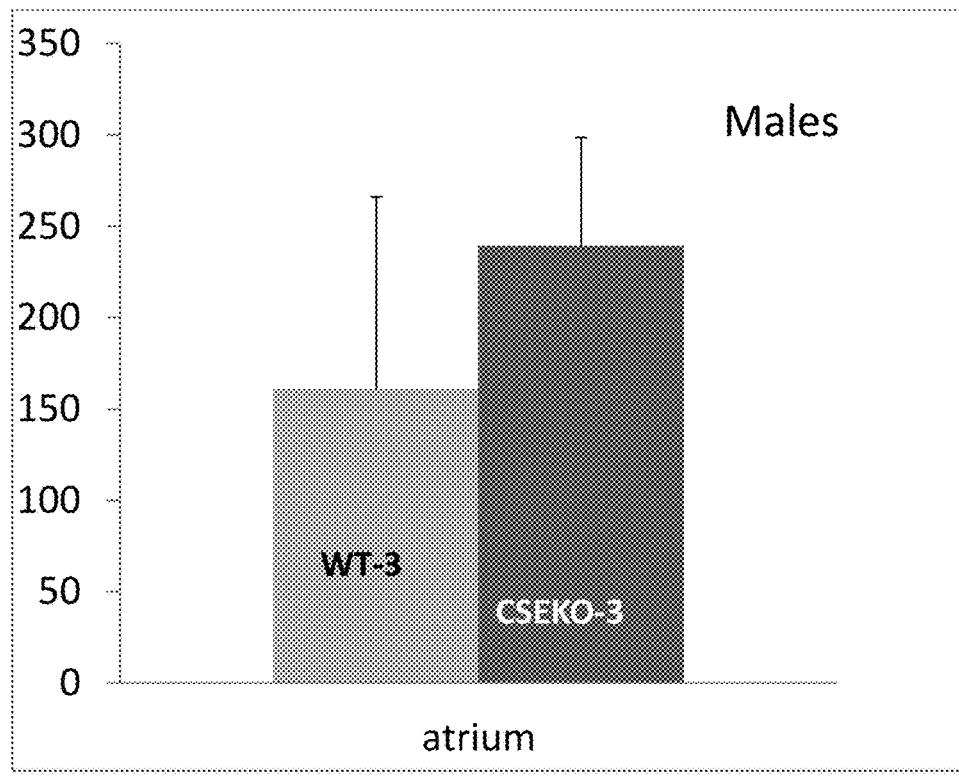
FIGS. 24A and 24B are bar graph showing NO levels in WT and CSE KO male (24A) and female (24B) mice in atria.
Figure 24B:
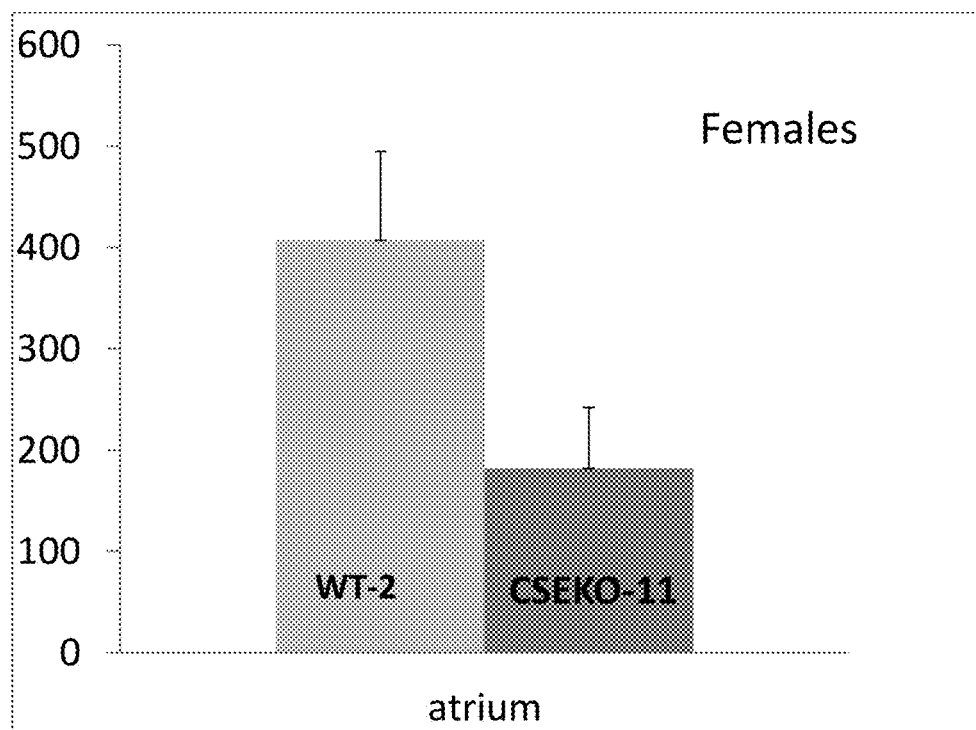

FIG. 23 shows NO levels in CSE KO mice atria are lower than WT mice. FIGS. 24A and 24B show gender variation in NO levels in CSE KO mice.

FIGS. 25A and 25B show Nitrite treatment reduced AF in female CSE KO mice.

Figure 26A:
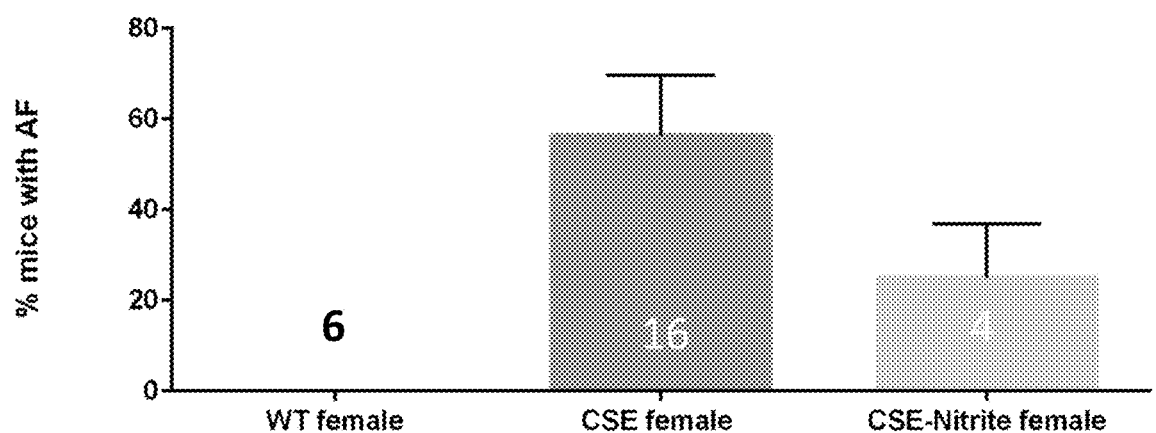
FIGS. 26A and 26B are bar graphs showing persistent AF (26A) and duration of any AF (26B) in WT female, CSE KO female, and CSE KO nitrite treated female mice.
Figure 26B:
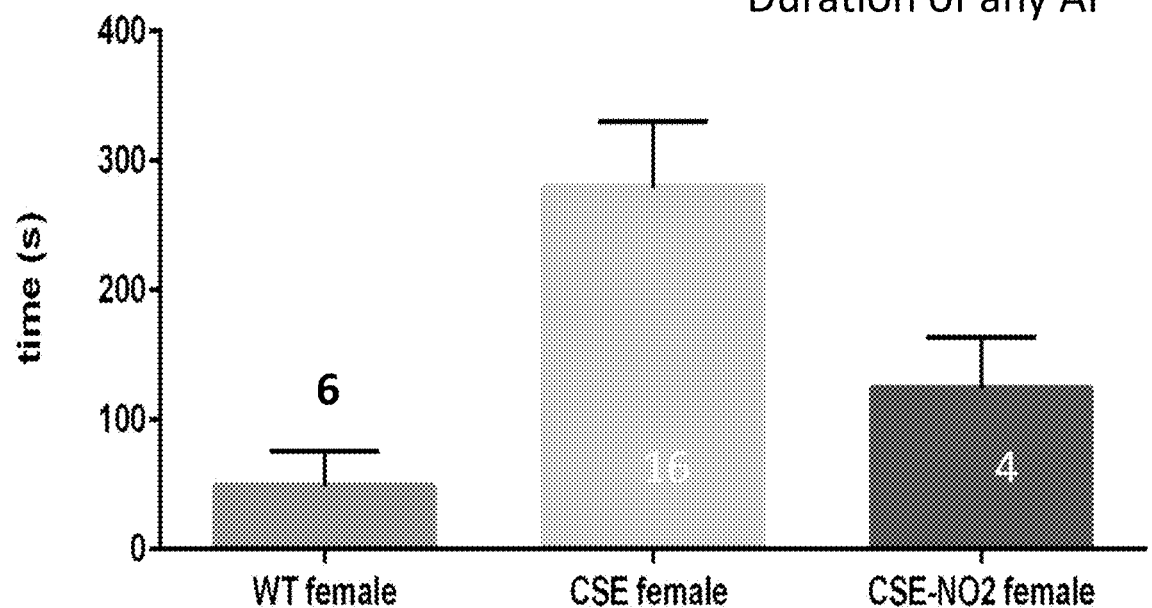

FIGS. 26A and 26B show that NO Reduced persistent AF in female mice.

Figure 27B:
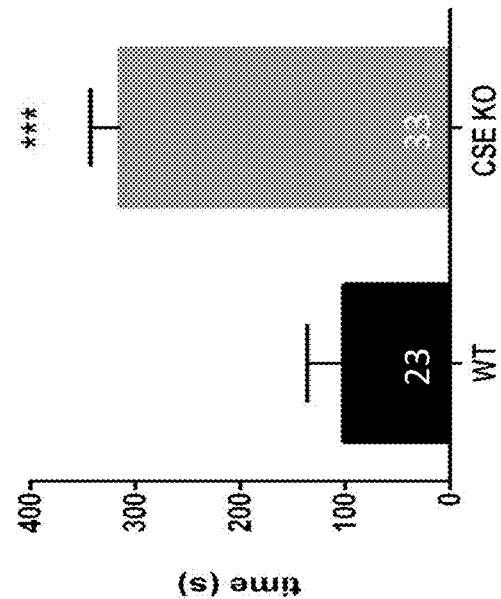
FIGS. 27A and 27B are bar graphs showing persistent AF (27A) and duration of any AF (27B) in WT and CSE KO mice.
Figure 27A:
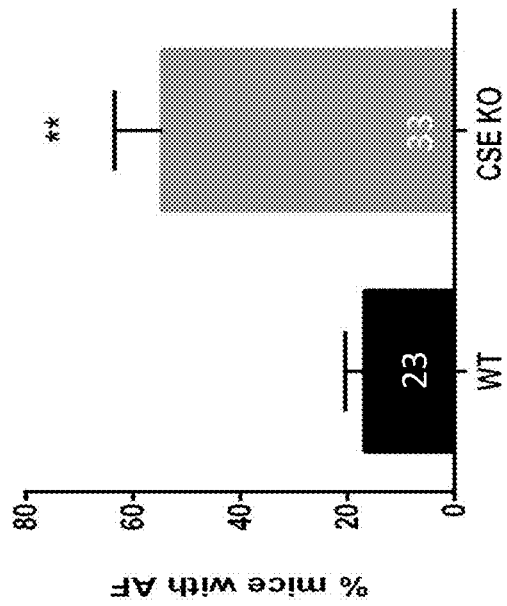
Figure 29B:
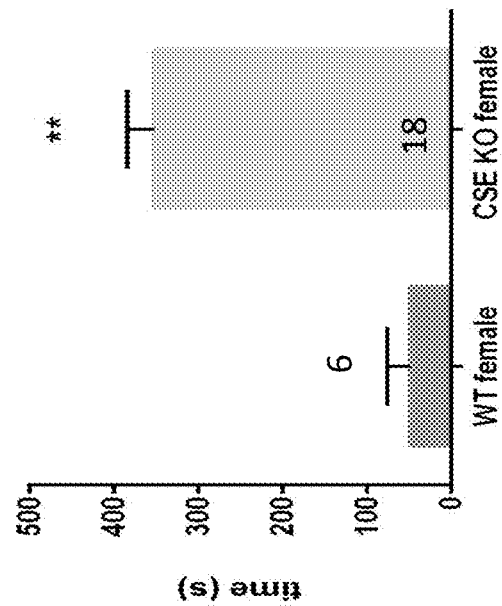
FIGS. 29A and 29B are bar graphs showing persistent AF (29A) and duration of any AF (29B) in WT and CSE KO female mice.
Figure 29A:
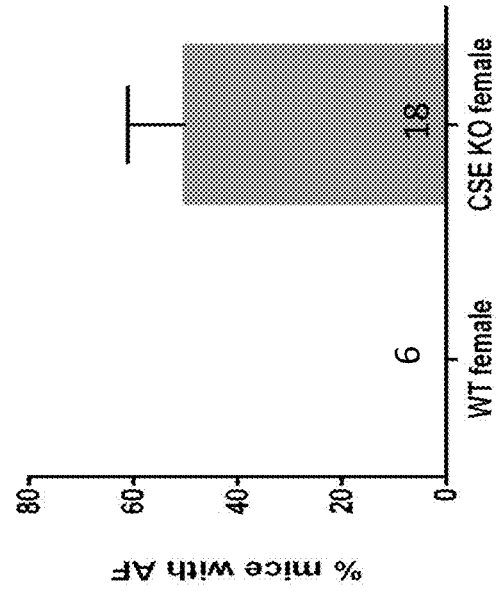

FIGS. 27A and 27B show that incidence and duration atrial fibrillation is increased in CSE KO mice.

FIGS. 28A to 29B show gender variations in AF in CSE KO mice.

Figure 30B:
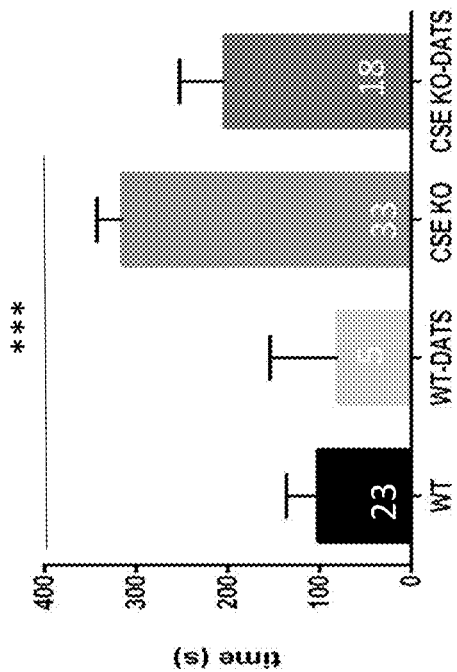
FIGS. 30A and 30B are bar graphs showing persistent AF (30A) and duration of any AF (30B) in WT, WT DATS treated, CSE KO, and CSE KO DATS treated mice.
Figure 30A:
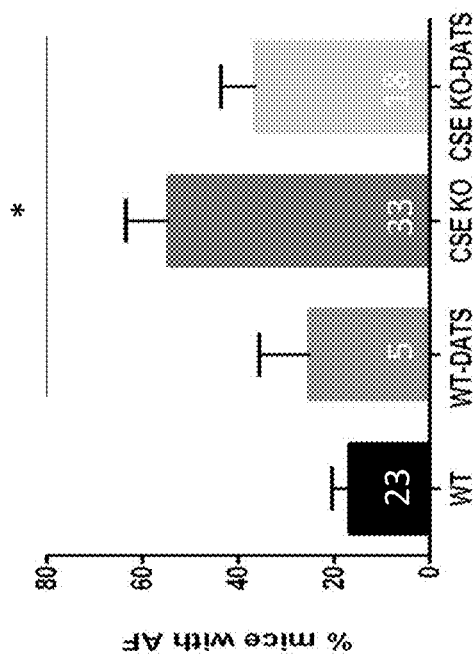
Figure 31B:
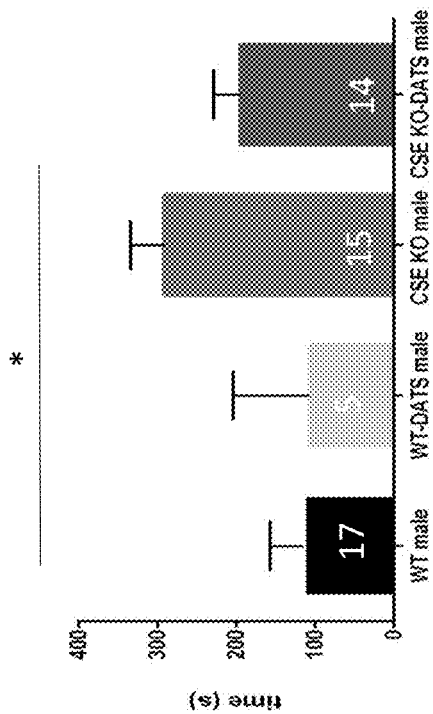
FIGS. 31A and 31B are bar graphs showing persistent AF (31A) and duration of any AF (31B) in WT male, WT DATS treated male, CSE KO male, and CSE KO DATS treated male mice.
Figure 31A:
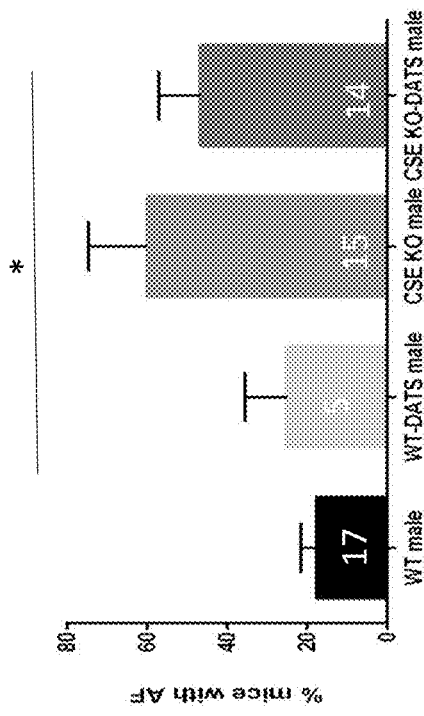
Figure 32B:
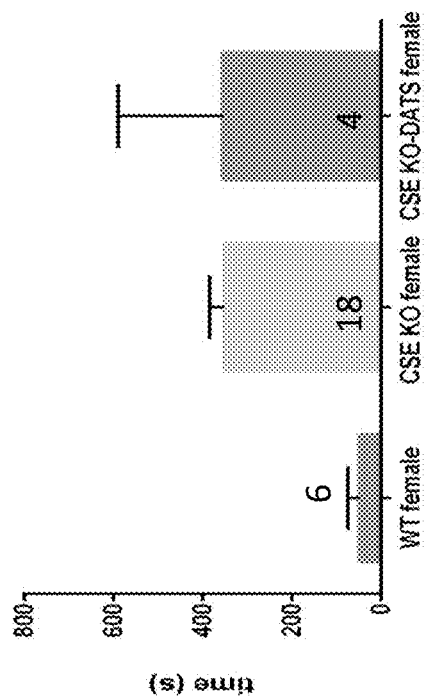
FIGS. 32A and 32B are bar graphs showing persistent AF (32A) and duration of any AF (32B) in WT female, CSE KO female, and CSE KO DATS treated female mice.
Figure 32A:
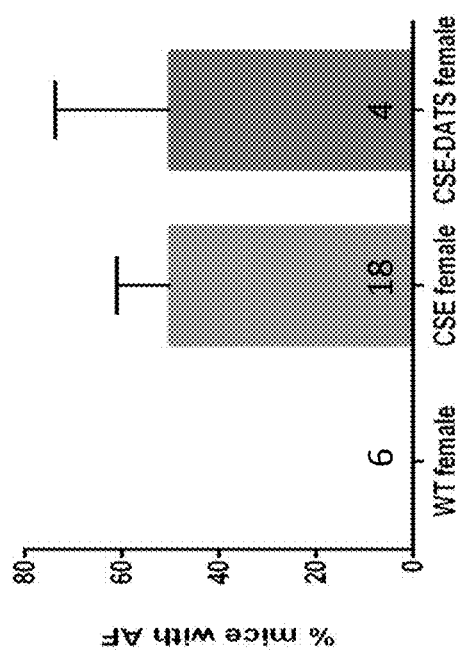

FIGS. 30A and 30B show DATS treatment and AF burden. FIGS. 31A to 32B show gender variations in response to DATS with CSE KO mice AF.

Figure 33B:
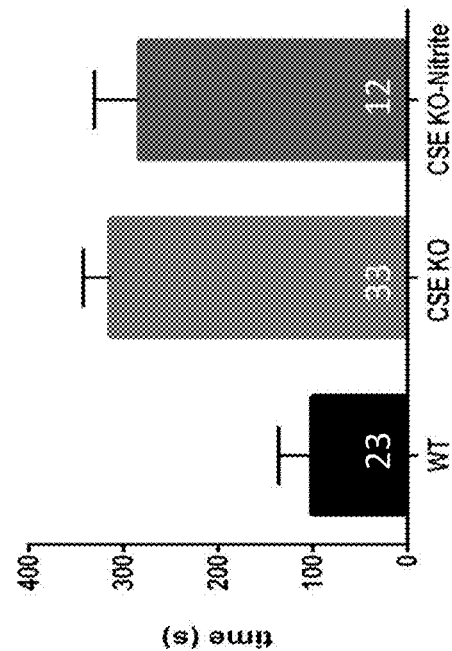
FIGS. 33A and 33B are bar graphs showing persistent AF (33A) and duration of any AF (33B) in WT, CSE KO, and CSE KO nitrite treated mice.
Figure 33A:
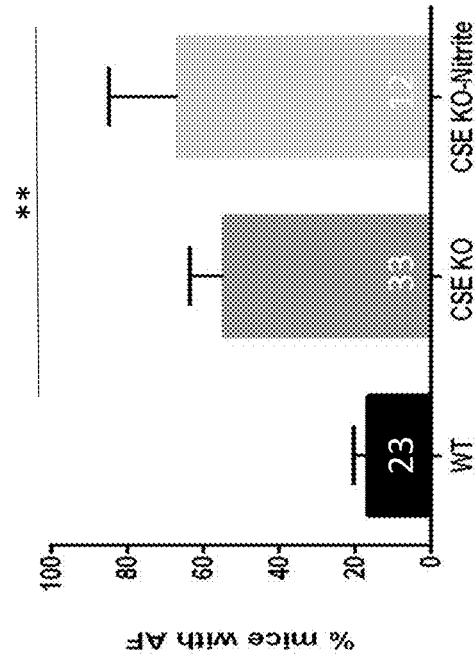
Figure 34B:
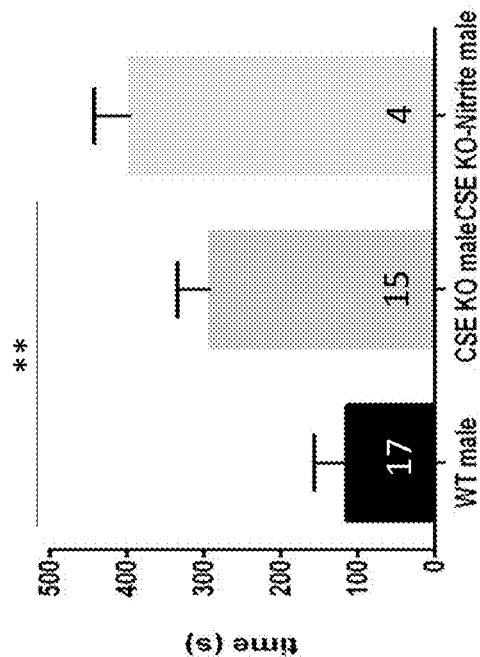
FIGS. 34A and 34B are bar graphs showing persistent AF (34A) and duration of any AF (34B) in WT male, CSE KO male, and CSE KO nitrite treated male mice.
Figure 34A:
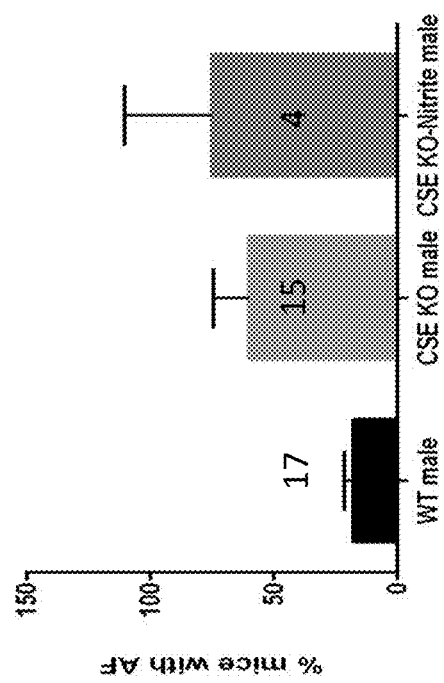
Figure 35A:
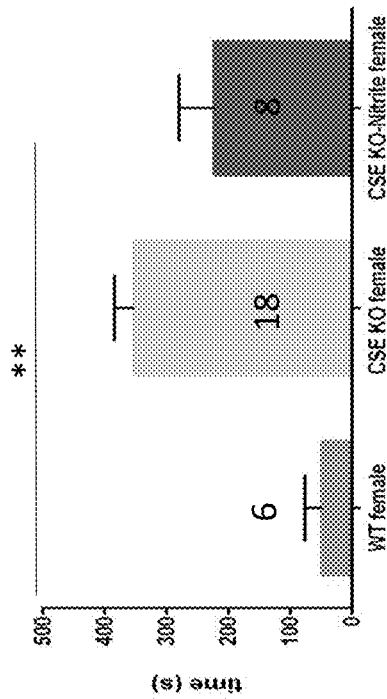
FIGS. 35A and 35B are bar graphs showing persistent AF (35A) and duration of any AF (35B) in WT female, CSE KO female, and CSE KO nitrite treated female mice.
Figure 35B:
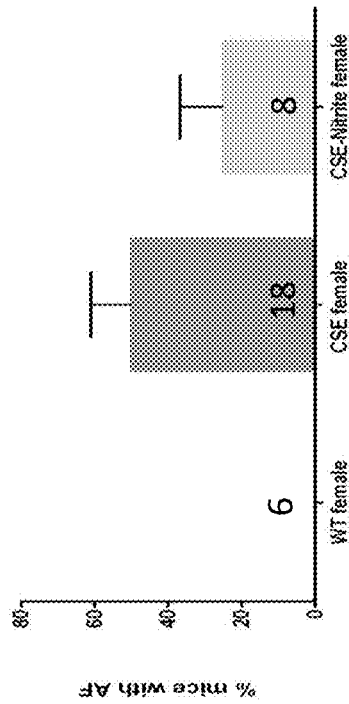

FIGS. 33A and 33B show Nitrite treatment and AF burden. FIGS. 34A to 35B show gender variations in response to Nitrite with CSE KO mice AF. Nitrite dramatically reduces persistent AF in female KO mice.

Figure 36B:
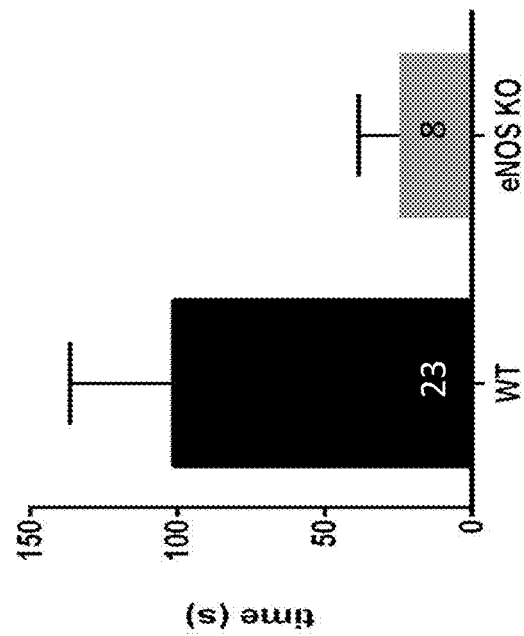
FIGS. 36A and 36B are bar graphs showing persistent AF (36A) and duration of any AF (36B) in WT and eNOS KO mice.
Figure 36A:
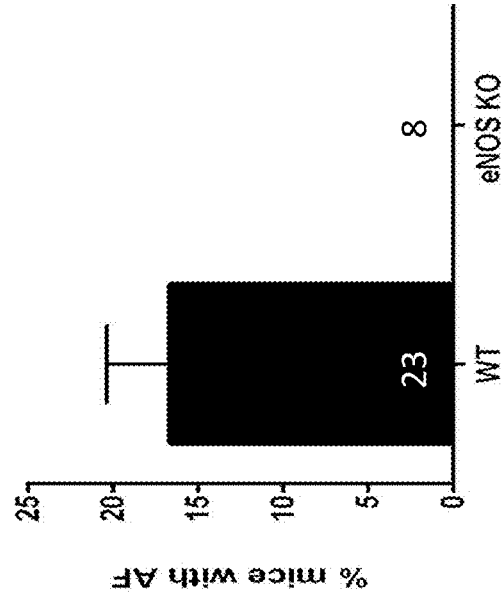

FIGS. 36A and 36B show AF incidence with eNOS KO mice.

Pharmaceutical Compositions

The methods described herein can also include the administrations of pharmaceutically acceptable compositions that include the therapeutic, or pharmaceutically acceptable salts, solvates, esters, amides, clathrates, stereoisomers, enantiomers, prodrugs or analogs thereof, or combination thereof. When employed as pharmaceuticals, any of the present compounds can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

This invention also includes pharmaceutical compositions which can contain one or more pharmaceutically acceptable carriers. In making the pharmaceutical compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, powders, lozenges, sachets, cachets, elixirs, suspensions, emulsions, solutions, syrups, and soft and hard gelatin capsules. As is known in the art, the type of diluent can vary depending upon the intended route of administration. The resulting compositions can include additional agents, such as preservatives.

The therapeutic agents of the invention can be administered alone, or in a mixture, in the presence of a pharmaceutically acceptable excipient or carrier. The excipient or carrier is selected on the basis of the mode and route of administration. Suitable pharmaceutical carriers, as well as pharmaceutical necessities for use in pharmaceutical formulations, are described in *Remington: The Science and Practice of Pharmacy,* $22^{nd}$ Ed., Gennaro, Ed., Lippencott Williams & Wilkins (2012), a well-known reference text in this field, and in the USP/NF (United States Pharmacopeia and the National Formulary), each of which is incorporated by reference. In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Examples of suitable excipients are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. Other exemplary excipients are described in *Handbook of Pharmaceutical Excipients,* $8^{th}$ Edition, Sheskey et al., Eds., Pharmaceutical Press (2017), which is incorporated by reference.

The methods described herein can include the administration of a therapeutic, or prodrugs or pharmaceutical compositions thereof, or other therapeutic agents. Exemplary therapeutics include those that raise NO level in the atrium and raise H2S level in the atrium.

The pharmaceutical compositions can be formulated so as to provide immediate, extended, or delayed release of the active ingredient after administration to the patient by employing procedures known in the art.

The compositions can be formulated in a unit dosage form, each dosage containing, e.g., 0.1-500 mg of the active ingredient. For example, the dosages can contain from about 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg from to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 50 mg to about 100 mg of the active ingredient, from about 50 mg to about 300 mg, from about 50 mg to about 250 mg, from about 100 mg to about 300 mg, or, from about 100 mg to about 250 mg of the active ingredient. For preparing solid compositions such as tablets, the principal active ingredient is mixed with one or more pharmaceutical excipients to form a solid bulk formulation composition containing a homogeneous mixture of a compound of the present invention. When referring to these bulk formulation compositions as homogeneous, the active ingredient is typically dispersed evenly throughout the composition so that the composition can be readily subdivided into equally effective unit dosage forms such as tablets and capsules. This solid bulk formulation is then subdivided into unit dosage forms of the type described above containing from, for example, 0.1 to about 500 mg of the active ingredient of the present invention.

Compositions for Oral Administration

The pharmaceutical compositions contemplated by the invention include those formulated for oral administration ("oral dosage forms"). Oral dosage forms can be, for example, in the form of tablets, capsules, a liquid solution or suspension, a powder, or liquid or solid crystals, which contain the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Formulations for oral administration may also be presented as chewable tablets, as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Controlled release compositions for oral use may be constructed to release the active drug by controlling the dissolution and/or the diffusion of the active drug substance. Any of a number of strategies can be pursued in order to obtain controlled release and the targeted plasma concentration vs time profile. In one example, controlled release is obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner. Examples include single or multiple unit tablet or capsule compositions, oil solutions, suspensions, emulsions, microcapsules, microspheres, nanoparticles, patches, and liposomes. In certain embodiments, compositions include biodegradable, pH, and/or temperature-sensitive polymer coatings.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions suitable for oral mucosal administration (e.g., buccal or sublingual administration) include tablets, lozenges, and pastilles, where the active ingredient is formulated with a carrier, such as sugar, acacia, tragacanth, or gelatin and glycerine.

Coatings

The pharmaceutical compositions formulated for oral delivery, such as tablets or capsules of the present invention can be coated or otherwise compounded to provide a dosage form affording the advantage of delayed or extended release. The coating may be adapted to release the active drug substance in a predetermined pattern (e.g., in order to achieve a controlled release formulation) or it may be adapted not to release the active drug substance until after passage of the stomach, e.g., by use of an enteric coating (e.g., polymers that are pH-sensitive ("pH controlled release"), polymers with a slow or pH-dependent rate of swelling, dissolution or erosion ("time-controlled release"), polymers that are degraded by enzymes ("enzyme-controlled release" or "biodegradable release") and polymers that form firm layers that are destroyed by an increase in pressure ("pressure-controlled release")). Exemplary enteric coatings that can be used in the pharmaceutical compositions described herein include sugar coatings, film coatings (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or coatings based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose. Furthermore, a time delay material such as, for example, glyceryl monostearate or glyceryl distearate, may be employed.

For example, the tablet or capsule can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release.

When an enteric coating is used, desirably, a substantial amount of the drug is released in the lower gastrointestinal tract.

In addition to coatings that effect delayed or extended release, the solid tablet compositions may include a coating adapted to protect the composition from unwanted chemical changes (e.g., chemical degradation prior to the release of the active drug substance). The coating may be applied on the solid dosage form in a similar manner as that described in *Encyclopedia of Pharmaceutical Technology*, vols. 5 and 6, Eds. Swarbrick and Boyland, 2000.

Parenteral Administration

Within the scope of the present invention are also parenteral depot systems from biodegradable polymers. These systems are injected or implanted into the muscle or subcutaneous tissue and release the incorporated drug over extended periods of time, ranging from several days to several months. Both the characteristics of the polymer and the structure of the device can control the release kinetics which can be either continuous or pulsatile. Polymer-based parenteral depot systems can be classified as implants or microparticles. The former are cylindrical devices injected into the subcutaneous tissue whereas the latter are defined as spherical particles in the range of 10-100 µm. Extrusion, compression or injection molding are used to manufacture implants whereas for microparticles, the phase separation method, the spray-drying technique and the water-in-oil-in-water emulsion techniques are frequently employed. The most commonly used biodegradable polymers to form microparticles are polyesters from lactic and/or glycolic acid, e.g. poly(glycolic acid) and poly(L-lactic acid) (PLG/PLA microspheres). Of particular interest are in situ forming depot systems, such as thermoplastic pastes and gelling systems formed by solidification, by cooling, or due to the sol-gel transition, cross-linking systems and organogels formed by amphiphilic lipids. Examples of thermosensitive polymers used in the aforementioned systems include, N-isopropylacrylamide, poloxamers (ethylene oxide and propylene oxide block copolymers, such as poloxamer 188 and 407), poly(N-vinyl caprolactam), poly(siloethylene glycol), polyphosphazenes derivatives and PLGA-PEG-PLGA.

Mucosal Drug Delivery

Mucosal drug delivery (e.g., drug delivery via the mucosal linings of the nasal, rectal, vaginal, ocular, or oral cavities) can also be used in the methods described herein. Methods for oral mucosal drug delivery include sublingual administration (via mucosal membranes lining the floor of the mouth), buccal administration (via mucosal membranes lining the cheeks), and local delivery (Harris et al., *Journal of Pharmaceutical Sciences,* 81(1): 1-10, 1992).

Oral transmucosal absorption is generally rapid because of the rich vascular supply to the mucosa and allows for a rapid rise in blood concentrations of the therapeutic.

For buccal administration, the compositions may take the form of, e.g., tablets, lozenges, etc. formulated in a conventional manner. Permeation enhancers can also be used in buccal drug delivery. Exemplary enhancers include 23-lauryl ether, aprotinin, azone, benzalkonium chloride, cetylpyridinium chloride, cetyltrimethylammonium bromide, cyclodextrin, dextran sulfate, lauric acid, lysophosphatidylcholine, methol, methoxysalicylate, methyloleate, oleic acid, phosphatidylcholine, polyoxyethylene, polysorbate 80, sodium EDTA, sodium glycholate, sodium glycodeoxycholate, sodium lauryl sulfate, sodium salicylate, sodium taurocholate, sodium taurodeoxycholate, sulfoxides, and alkyl glycosides. Bioadhesive polymers have extensively been employed in buccal drug delivery systems and include cyanoacrylate, polyacrylic acid, hydroxypropyl methylcellulose, and poly methacrylate polymers, as well as hyaluronic acid and chitosan.

Liquid drug formulations (e.g., suitable for use with nebulizers and liquid spray devices and electrohydrodynamic (EHD) aerosol devices) can also be used. Other methods of formulating liquid drug solutions or suspension suitable for use in aerosol devices are known to those of skill in the art (see, e.g., Biesalski, U.S. Pat. No. 5,112,598, and Biesalski, U.S. Pat. No. 5,556,611).

Formulations for sublingual administration can also be used, including powders and aerosol formulations. Exemplary formulations include rapidly disintegrating tablets and liquid-filled soft gelatin capsules.

Dosing Regimes

The present methods for treating AF or a pre-AF state are carried out by administering a therapeutic for a time and in an amount sufficient to result in increased level of H2S and/or increased level of NO in the atrium.

The amount and frequency of administration of the compositions can vary depending on, for example, what is being administered, the state of the patient, and the manner of administration. In therapeutic applications, compositions can be administered to a patient suffering from AF or a pre-AF state in an amount sufficient to relieve or least partially relieve the symptoms of the AF or a pre-AF state and its complications. The dosage is likely to depend on such variables as the type and extent of progression of the AF or a pre-AF state, the severity of the AF or a pre-AF state, the age, weight and general condition of the particular patient, the relative biological efficacy of the composition selected, formulation of the excipient, the route of administration, and the judgment of the attending clinician. Effective doses can be extrapolated from dose-response curves derived from in vitro or animal model test system. An effective dose is a dose that produces a desirable clinical outcome by, for example, improving a sign or symptom of the AF or a pre-AF state or slowing its progression.

The amount of therapeutic per dose can vary. For example, a subject can receive from about 0.1 µg/kg to about 10,000 µg/kg. Generally, the therapeutic is administered in an amount such that the peak plasma concentration ranges from 150 nM-250 µM.

Exemplary dosage amounts can fall between 0.1-5000 µg/kg, 100-1500 µg/kg, 100-350 µg/kg, 340-750 µg/kg, or 750-1000 µg/kg. Exemplary dosages can 0.25, 0.5, 0.75, 1°, or 2 mg/kg. In another embodiment, the administered dosage can range from 0.05-5 mmol of therapeutic (e.g., 0.089-3.9 mmol) or 0.1-50 µmol of therapeutic (e.g., 0.1-25 µmol or 0.4-20 µmol).

The plasma concentration of therapeutic can also be measured according to methods known in the art. Exemplary peak plasma concentrations of therapeutic can range from 0.05-10 µM, 0.1-10 µM, 0.1-5.0 µM, or 0.1-1 µM. Alternatively, the average plasma levels of therapeutic can range from 400-1200 µM (e.g., between 500-1000 µM) or between 50-250 µM (e.g., between 40-200 µM). In some embodiments where sustained release of the drug is desirable, the peak plasma concentrations (e.g., of therapeutic) may be maintained for 6-14 hours, e.g., for 6-12 or 6-10 hours. In other embodiments where immediate release of the drug is desirable, the peak plasma concentration (e.g., of therapeutic) may be maintained for, e.g., 30 minutes.

The frequency of treatment may also vary. The subject can be treated one or more times per day with therapeutic (e.g., once, twice, three, four or more times) or every so-many hours (e.g., about every 2, 4, 6, 8, 12, or 24 hours). Preferably, the pharmaceutical composition is administered 1 or 2 times per 24 hours. The time course of treatment may be of varying duration, e.g., for two, three, four, five, six, seven, eight, nine, ten or more days. For example, the treatment can be twice a day for three days, twice a day for seven days, twice a day for ten days. Treatment cycles can be repeated at intervals, for example weekly, bimonthly or monthly, which are separated by periods in which no treatment is given. The treatment can be a single treatment or can last as long as the life span of the subject (e.g., many years).

Kits

Any of the pharmaceutical compositions of the invention described herein can be used together with a set of instructions, i.e., to form a kit. The kit may include instructions for use of the pharmaceutical compositions as a therapy as described herein. For example, the instructions may provide dosing and therapeutic regimes for use of the compounds of the invention to reduce symptoms and/or underlying cause of the AF or a pre-AF state.

The invention illustratively disclosed herein suitably may explicitly be practiced in the absence of any element which is not specifically disclosed herein. While various embodiments of the present invention have been described in detail, it is apparent that various modifications and alterations of those embodiments will occur to and be readily apparent those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways.

In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items while only the terms "consisting of" and "consisting only of" are to be construed in the limitative sense.

We claim:

1. A method of treating atrial fibrillation or a pre-atrial fibrillation condition in a mammal comprising: administering a pharmaceutical composition containing therapeutically effective amount of both diallyl trisulfide (DATS), and an inorganic nitrite, or a pharmacologically acceptable salt thereof; and formulating a relative level of diallyl trisulfide and nitrite in the pharmaceutical composition based on if the mammal is a male or female.

2. The method of claim 1 wherein the mammal is a male.

3. The method of claim 1 wherein the inorganic nitrite is one of ammonium nitrite ($NH_4NO_2$), barium nitrite ($Ba(NO_2)_2$), calcium nitrite ($Ca(NO_2)_2$), cesium nitrite ($CsNO_2$), cobalt(II)nitrite ($Co(NO_2)_2$), cobalt(III)potassium nitrite ($CoK_3(NO_2)_6$), lithium nitrite ($LiNO_2$), magnesium nitrite ($MgNO_2$), potassium nitrite ($KNO_2$), rubidium nitrite ($RbNO_2$), silver(I)nitrite ($AgNO_2$), strontium nitrite ($Sr(NO_2)_2$), and zinc nitrite ($Zn(NO_2)_2$), and wherein the inorganic nitrite is in one of a anhydrous and hydrated form.

4. The method of claim 1 wherein the inorganic nitrite is sodium nitrite.

5. The method of claim 1 wherein the mammal is a female.

6. The method of claim 1 wherein the mammal is a human.

7. The method of claim 1 wherein the pharmaceutical composition has a higher level of diallyl trisulfide to nitrite if the mammal is a male and has a lower level of sulfide to nitrite if the mammal is a female.

8. A pharmaceutical composition for treating atrial fibrillation or a pre-atrial fibrillation condition comprising; a therapeutically effective dose of diallyl trisulfide, and a therapeutically effective dose of inorganic nitrite, or a pharmacologically acceptable salt thereof.

9. The pharmaceutical composition of claim 8 wherein the inorganic nitrite is one of ammonium nitrite ($NH_4NO_2$), barium nitrite ($Ba(NO_2)_2$), calcium nitrite ($Ca(NO_2)_2$), cesium nitrite ($CsNO_2$), cobalt(II)nitrite ($Co(NO_2)_2$), cobalt (III)potassium nitrite ($CoK_3(NO_2)_6$), lithium nitrite ($LiNO_2$), magnesium nitrite ($MgNO_2$), potassium nitrite ($KNO_2$), rubidium nitrite ($RbNO_2$), silver(I)nitrite ($AgNO_2$), strontium nitrite ($Sr(NO_2)_2$), and zinc nitrite ($Zn(NO_2)_2$), and wherein the inorganic nitrite is in one of a anhydrous and hydrated form.

10. The pharmaceutical composition of claim 8 wherein the inorganic nitrite is sodium nitrite.

* * * * *